United States Patent
Lu

(10) Patent No.: US 12,398,387 B2
(45) Date of Patent: Aug. 26, 2025

(54) COMPOSITIONS AND METHODS FOR PREPARING FACTOR Xa AND DERIVATIVES

(71) Applicant: Alexion Pharmaceuticals, Inc., Boston, MA (US)

(72) Inventor: Genmin Lu, South San Francisco, CA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 761 days.

(21) Appl. No.: 17/629,999

(22) PCT Filed: Aug. 5, 2020

(86) PCT No.: PCT/US2020/045039
§ 371 (c)(1),
(2) Date: Jan. 25, 2022

(87) PCT Pub. No.: WO2021/026254
PCT Pub. Date: Feb. 11, 2021

(65) Prior Publication Data
US 2022/0251534 A1    Aug. 11, 2022

Related U.S. Application Data

(60) Provisional application No. 62/990,885, filed on Mar. 17, 2020, provisional application No. 62/884,652, filed on Aug. 8, 2019.

(51) Int. Cl.
*C12N 9/64* (2006.01)
(52) U.S. Cl.
CPC ........ *C12N 9/6432* (2013.01); *C07K 2319/31* (2013.01); *C07K 2319/50* (2013.01)

(58) Field of Classification Search
CPC .............. C12N 9/6432; C07K 2319/31; C07K 2319/50
See application file for complete search history.

(56) References Cited

U.S. PATENT DOCUMENTS

| | | | |
|---|---|---|---|
| 2009/0098119 A1 | 4/2009 | Lu et al. | |
| 2015/0184142 A1 | 7/2015 | Hong et al. | |
| 2015/0239929 A1* | 8/2015 | Lu ........................ | C12N 9/6432 435/226 |
| 2016/0115234 A1 | 4/2016 | Salas et al. | |
| 2017/0240879 A1 | 8/2017 | Lu et al. | |

FOREIGN PATENT DOCUMENTS

| | | |
|---|---|---|
| FR | 3077296 A1 | 8/2019 |
| WO | WO 2006/128668 A2 | 12/2006 |
| WO | WO 2009/042962 A2 | 4/2009 |
| WO | WO 2010/117729 A1 | 10/2010 |
| WO | WO 2017/147522 A1 | 8/2017 |

OTHER PUBLICATIONS

International Search Report and Written Opinion dated Feb. 1, 2021 for PCT/US2020/045039. (16 pages).
European Search Report and Opinion dated Nov. 17, 2023 for EP Application No. 20851033.9. 9 pages.

* cited by examiner

*Primary Examiner* — Li N Komatsu
(74) *Attorney, Agent, or Firm* — Sheppard Mullin Richter & Hampton LLP

(57) ABSTRACT

The present disclosure relates to protein sequences which can be used to generate factor Xa proteins and derivatives thereof. The protein sequences include a factor Xa light chain portion, a heavy chain catalytic domain portion, and an activation peptide C-terminal to the heavy chain catalytic domain portion.

14 Claims, 6 Drawing Sheets
Specification includes a Sequence Listing.

| Name | SEQ ID NO: |
|---|---|
| AnXa precursor | 4 |
| C01 | 18 |
| C02 | 19 |
| C03 | 20 |
| C04 | 21 |
| C05 | 22 |
| C06 | 23 |
| C07 | 24 |
| C08 | 25 |
| C09 | 26 |
| C10 | 27 |
| C11 | 28 |
| C12 | 41 |
| C13 | 42 |
| C14 | 43 |

FIG. 1

COMPOSITIONS AND METHODS FOR PREPARING FACTOR Xa AND DERIVATIVES

CROSS REFERENCE TO RELATED APPLICATIONS

This application is the United States National Phase Application of PCT/US2020/045039, filed Aug. 5, 2020, and claims the benefit under 35 U.S.C. § 119 (e) of U.S. Provisional Application Ser. No. 62/884,652, filed Aug. 8, 2019, and 62/990,885, filed Mar. 17, 2020, the content of each of which is incorporated by reference in its entirety into the present disclosure.

SEQUENCE LISTING

The instant application contains a Sequence Listing which has been submitted electronically in ASCII format and is hereby incorporated by reference in its entirety. Said ASCII copy, created on Sep. 11, 2020, is named 37JE-267815-WO_SL.txt and is 138,454 bytes in size.

BACKGROUND

Recombinant factor Xa (fXa) and its derivatives, such as Andexanet alfa, can be made from host mammalian cell lines. Andexanet alfa (or simply Andexanet) is a drug that has been approved in the U.S. and Europe for patients treated with rivaroxaban or apixaban, when reversal of anticoagulation is needed due to life-threatening or uncontrolled bleeding. Rivaroxaban and apixaban are factor Xa inhibitors, a group of anticoagulant (anti-blood clotting) drugs that also include betrixaban and edoxaban, as well as low molecular weight heparins (LMWHs). Andexanet is a modified recombinant derivative of factor Xa (fXa). It acts as a decoy molecule, and binds to the inhibitor and relives its inhibition of fXa, thus restores normal coagulation activity of fXa.

Factor Xa, as well as Andexanet, have two chains linked by a disulfide bond between the two chains. Recombinant native fXa is usually made first with expression of an inactive precursor factor X (fX), followed by a second step of activating the expressed fX to fXa by physiologic enzymes (e.g., FVIIa/TF, FIXa/FVIIIa) or by non-physiologic activators (e.g., RVV-X). The difference between fX and fXa is the removal of a 52 amino acid residues of the activation peptide (AP) at the N-terminus of the fX heavy chain. The activation step is necessary for converting the inactive fX to the native fXa, because the typical production cell line, e.g., CHO cell, is unable to process and remove the AP.

In contrast, andexanet is directly expressed as a fully processed and functional molecule that can be purified directly from the harvested cell culture fluid. This is accomplished by replacing the AP sequence in the native fX with a —RKR— tripeptide to form a —RKRRKR— (SEQ ID NO: 7) linker between the heavy- and light-chains, which can be processed by the CHO cells.

SUMMARY

The present disclosure provides composition and methods for preparing two-chain, activated, factor Xa proteins or the derivatives thereof. It is discovered that when an activation peptide (AP) is fused to the C-terminal end of the heavy chain of the factor Xa protein or derivative, the resulting protein can be more efficiently expressed, and the attachment of the activation peptide (AP) to the heavy chain does not affect the activity of the protein. By contrast, adding the activation peptide to the other parts of the protein is either not useful in enhancing expression (e.g. when attached to the C-terminus of the light chain) or even presents challenges for manufacturing (e.g. when attached to the N-terminus of the heavy chain). Further, contrary to the conventional wisdom (see, e.g., Branchini et al, *J Thromb Haemost* 2015; 13:1468-74, and Ferrarese et al., Thrombosis Res. 2019, 173:4-11) that the removal of the C-terminal 20 amino acid residues of FX heavy chain (the beta peptide) does not negatively impact the protein expression of factor X, it is discovered herein that such a large truncation is not desired for efficient expression of fXa and derivatives. More surprisingly, the impact of C-terminal truncation on protein expressions can be rescued by fusing the AP to the C-terminal of FXa and derivatives thereof.

In one embodiment, the present disclosure provides a protein comprising the amino acid sequence of the formula (I) of:

LC-L1-HC-L2-AP          (I)

wherein:
  LC comprises the amino acid sequence of SEQ ID NO:13 or a peptide having at least 85% sequence identity to SEQ ID NO:13,
  L1 is a peptide linker comprising a protease recognition site,
  HC comprises the amino acid sequence of SEQ ID NO:11 or a peptide having at least 85% sequence identity to SEQ ID NO:11,
  L2 is absent or is a peptide linker that cannot be processed by the protease, and
  AP comprises an activation peptide,
  wherein the protein is capable of, when the L1 is processed by the protease, producing a two-chain polypeptide comprising the LC and HC on separate chains connected by a disulfide bound, wherein the two-chain polypeptide is capable of binding to a factor Xa inhibitor.

In another embodiment, provided is a protein comprising the amino acid sequence of the formula (II) of:

HSA-L2-LC-L1-HC          (II)

wherein:
  HSA is a human serum albumin (HSA) or a variant having at least 85% sequence identity to the HSA;
  L1 is a peptide linker comprising a protease recognition site;
  L2 is absent or is a peptide linker that cannot be processed by the protease;
  LC comprises the amino acid sequence of SEQ ID NO:13 or a peptide having at least 85% sequence identity to SEQ ID NO:13; and
  HC comprises the amino acid sequence of SEQ ID NO:11 or a peptide having at least 85% sequence identity to SEQ ID NO:11,
  wherein the protein is capable to, when the L1 is processed by the protease, produce a two-chain polypeptide comprising the LC and HC on separate chains, wherein the two-chain polypeptide is capable of binding to a factor Xa inhibitor.

In another embodiment, provided is a protein comprising the amino acid sequence of the formula (II) of:

LC-L1-HC-L2-HSA          (III)

wherein:
  HSA is a human serum albumin (HSA) or a variant having at least 85% sequence identity to the HSA;
  L1 is a peptide linker comprising a protease recognition site;
  L2 is absent or is a peptide linker that cannot be processed by the protease;
  LC comprises the amino acid sequence of SEQ ID NO:13 or a peptide having at least 85% sequence identity to SEQ ID NO:13; and HC comprises the amino acid sequence of SEQ ID NO:11 or a peptide having at least 85% sequence identity to SEQ ID NO:11,
wherein the protein is capable to, when the L1 is processed by the protease, produce a two-chain polypeptide comprising the LC and HC on separate chains, wherein the two-chain polypeptide is capable of binding to a factor Xa inhibitor.

In some embodiments, the LC does not include amino acid residues 1-45 of SEQ ID NO: 2. In some embodiments, L2 is absent.

Also provided, in some embodiments, is a two-chain polypeptide comprising a light chain that comprises the amino acid sequence of SEQ ID NO:13 or a peptide having at least 85% sequence identity to SEQ ID NO:13, and a heavy chain that comprises a first fragment comprising the amino acid sequence of SEQ ID NO:11 or a peptide having at least 85% sequence identity to SEQ ID NO:11, and a second fragment that is a the C-terminal side of the first fragment and comprises an activation peptide, wherein the two-chain polypeptide is capable of binding to a factor Xa inhibitor.

Also provided is a two-chain polypeptide comprising a light chain that comprises a first fragment comprising a human serum albumin (HSA) or a variant having at least 85% sequence identity to the HSA, and a second fragment comprising the amino acid sequence of SEQ ID NO: 13 or a peptide having at least 85% sequence identity to SEQ ID NO:13, and a heavy chain that comprises the amino acid sequence of SEQ ID NO:11 or a peptide having at least 85% sequence identity to SEQ ID NO:11, wherein the two-chain polypeptide is capable of binding to a factor Xa inhibitor, and wherein the light chain does not include amino acid residues 1-45 of SEQ ID NO:2.

Polynucleotides, cells transfected with the polynucleotides, and methods are also provided, in some embodiments, to prepare the two-chain polypeptides.

BRIEF DESCRIPTION OF THE DRAWINGS

FIG. 1 illustrates the structures of constructs C01-C14.

DETAILED DESCRIPTION

I. Definitions

Figure 2A:
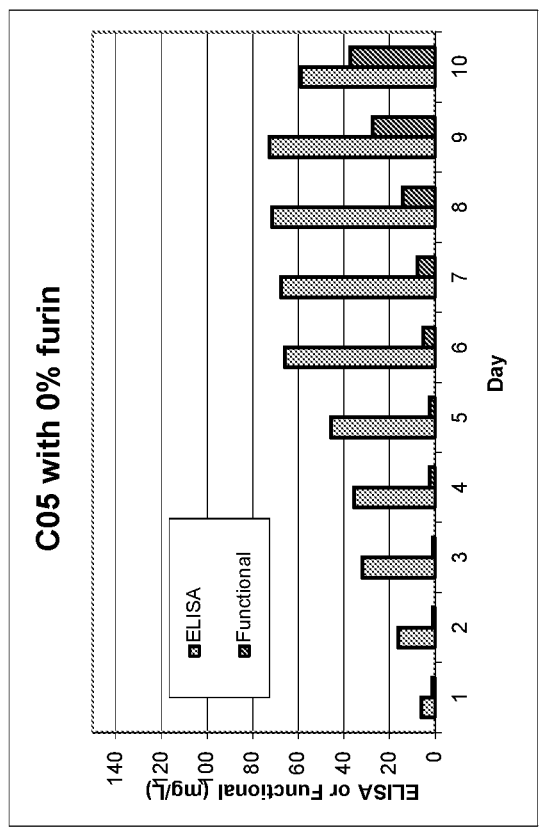
FIG. 2A-2D show the expression and activity testing results for C05 (2A), C07 (2B), C08 (2C) and C10 (2D).
Figure 2A:
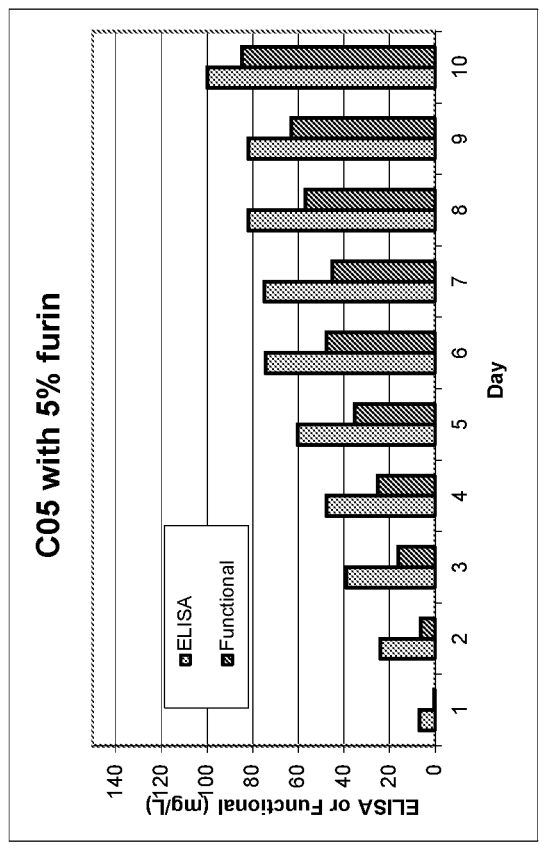
Figure 2B:
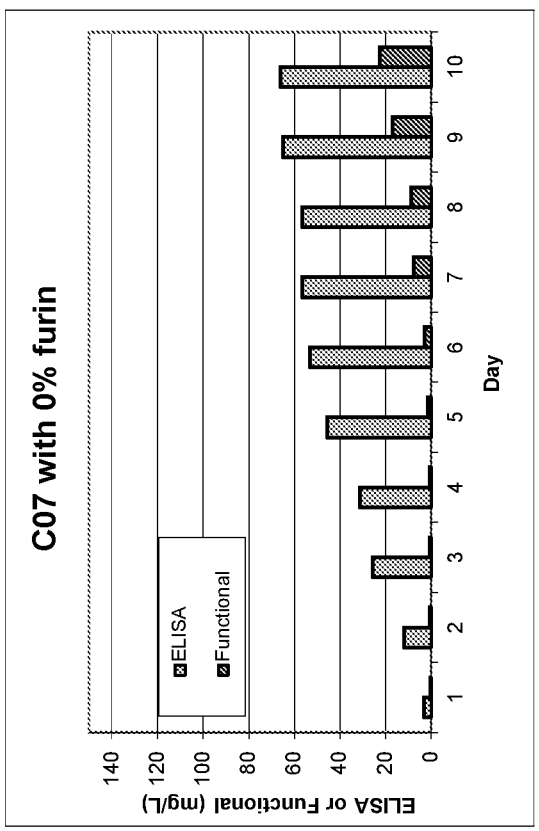
Figure 2B:
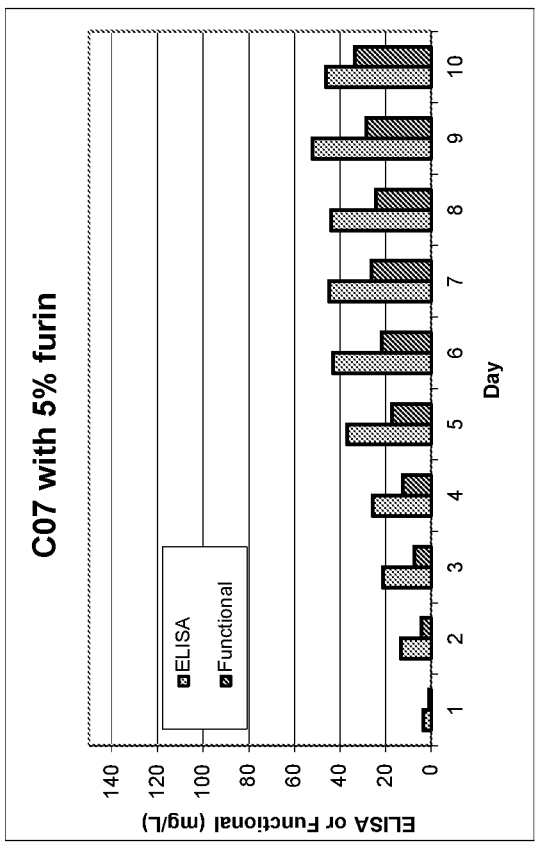
Figure 2C:
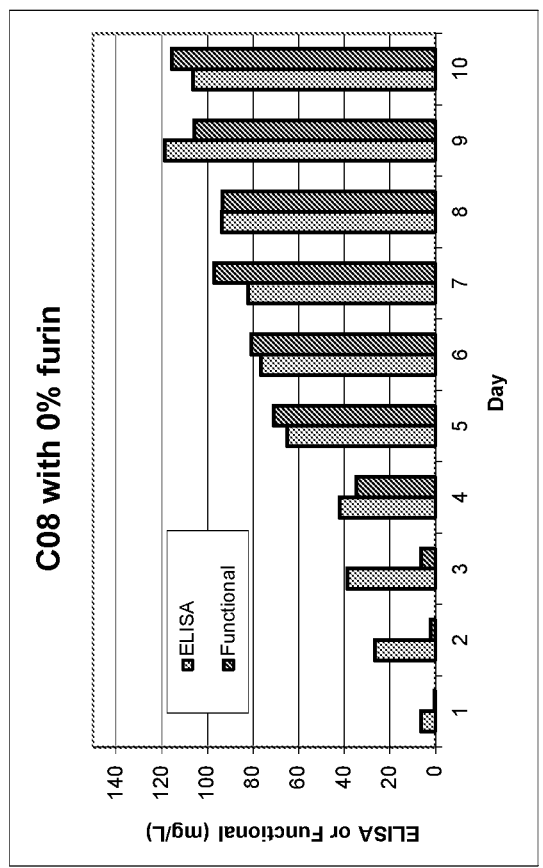
Figure 2C:
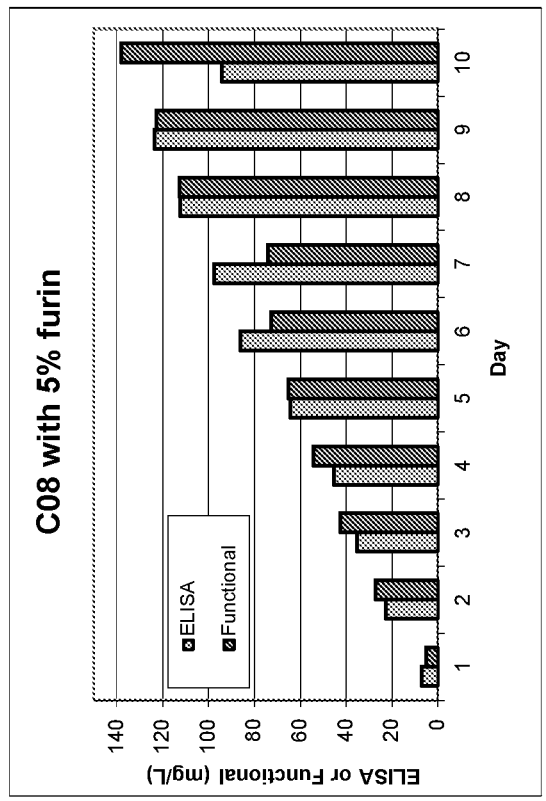
Figure 2D:
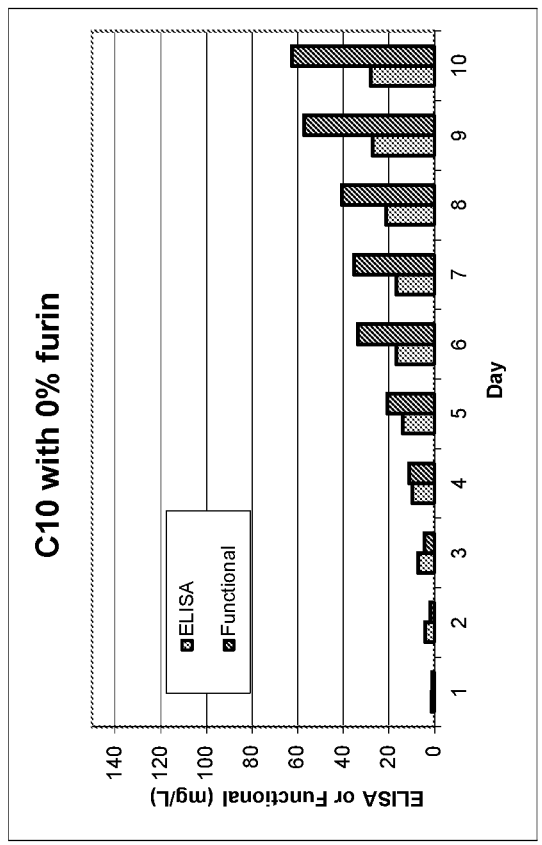
Figure 2D:
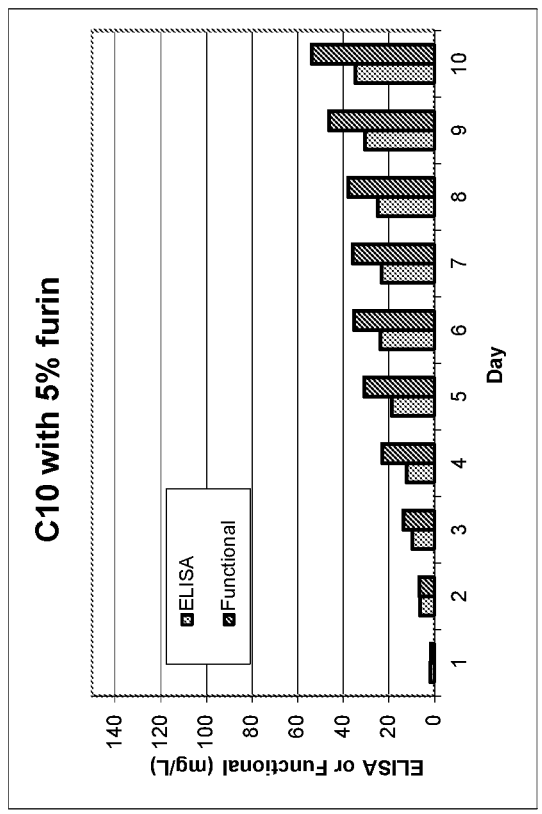

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. Single letter and three letter abbreviations of the naturally occurring amino acids are listed below. A peptide of three or more amino acids is commonly called an oligopeptide if the peptide chain is short. If the peptide chain is long, the peptide is commonly called a polypeptide or a protein.

"Factor Xa" or "fXa" or "fXa protein" refers to a serine protease in the blood coagulation pathway, which is produced from the inactive factor X (fX). Factor Xa is activated by either factor IXa with its cofactor, factor VIIIa, in a complex known as intrinsic Xase, or factor VIIa with its cofactor, tissue factor, in a complex known as extrinsic Xase. fXa forms a membrane-bound prothrombinase complex with factor Va and is the active component in the prothrombinase complex that catalyzes the conversion of prothrombin to thrombin. Thrombin is the enzyme that catalyzes the conversion of fibrinogen to fibrin, which ultimately leads to blood clot formation. Thus, the biological activity of fXa is sometimes referred to as "procoagulant activity" herein.

Factor Xa is a two chain molecule linked by one disulfide bond between the two chains. The light chain (LC) has 139 amino acid (amino acids 1 through 139 of SEQ ID NO:2) residues and contains the γ-carboxyglutamic acid (Gla)-rich domain (amino acids 1-45 of SEQ ID NO:2), including a short aromatic stack (AS) (amino acids 40-45 of SEQ ID NO:2), followed by two epidermal growth factor (EGF)-like domains (EGF1: amino acids 46-84, EGF2: amino acids 85-128 of SEQ ID NO:2).

The heavy chain (HC), prior to activation, has 306 amino acids and contains a 52 amino acids activation peptide (AP: amino acids 143-194 of SEQ ID NO:2) followed by the catalytic domain (amino acids 195-448 of SEQ ID NO:2). The catalytic triad equivalents to H57-D102-S195 in chymotrypsin numbering are located at His236, Asp282, and Ser379 in the fX sequence (SEQ ID NO:2) (amino acids 236, 282 and 379 of SEQ ID NO:2). The heavy chain contains the serine protease, trypsin-like active site and the N-terminal activation peptide which is glycosylated. The heavy chain has at least three forms, α, β, and γ, which differ due to the cleavage of a C-terminal peptide in the heavy chain.

The nucleotide sequence coding human factor X ("fX") can be found in GenBank, "NM_000504". The corresponding amino acid sequence and domain structure of fX are described in Leytus et al, *Biochemistry*, 1986, 25:5098-5102. The domain structure of mature fX is also described in Venkateswarlu, D. et al, *Biophysical Journal*, 2002, 82:1190-1206. Upon catalytic cleavage of the first 52 residues of the heavy chain, fX is activated to fXa (SEQ ID NO: 3). FXa contains a light chain with post-translation of glutamic acid residues to gamma-carboxyglutamic acid) and a heavy chain. The first 45 amino acid residues of the light chain is called the Gla domain because it contains 11 post-translationally modified γ-carboxyglutamic acid residues (Gla). It also contains a short (6 amino acid residues) aromatic stack sequence. Chymotrypsin digestion selectively removes the 1-44 residues resulting in Gla-domainless fXa. The serine protease catalytic domain of fXa locates at the C-terminal heavy chain. The heavy chain of fXa is highly homologous to other serine proteases such as thrombin, trypsin, and activated protein C.

TABLE 1

Polypeptide Sequence of Human Factor X (SEQ ID NO: 1)

```
  1 MGRPLHLVLL SASLAGLLLL GESLFIRREQ ANNILARVTR ANSFLEEMKK GHLERECMEE
 61 TCSYEEAREV FEDSDKTNEF WNKYKDGDQC ETSPCQNQGK CKDGLGEYTC TCLEGFEGKN
121 CELFTRKLCS LDNGDCDQFC HEEQNSVVCS CARGYTLADN GKACIPTGPY PCGKQTLERR
181 KRSVAQATSS SGEAPDSITW KPYDAADLDP TENPFDLLDF NQTQPERGDN NLTRIVGGQE
241 CKDGECPWQA LLINEENEGF CGGTILSEFY ILTAAHCLYQ AKRFKVRVGD RNTEQEEGGE
301 AVHEVEVVIK HNRFTKETYD FDIAVLRLKT PITFRMNVAP ACLPERDWAE STLMTQKTGI
361 VSGFGRTHEK GRQSTRLKML EVPYVDRNSC KLSSSFIITQ NMFCAGYDTK QEDACQGDSG
421 GPHVTRFKDT YFVTGIVSWG EGCARKGKYG IYTKVTAFLK WIDRSMKTRG LPKAKSHAPE
481 VITSSPLK
```

TABLE 2

Polypeptide Sequence of Mature Human Factor X (SEQ ID NO: 2)

```
  1 ANSFLEEMKK GHLERECMEE TCSYEEAREV FEDSDKTNEF WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLERR KRSVAQATSS SGEAPDSITW KPYDAADLDP TENPFDLLDF
181 NQTQPERGDN NLTRIVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDSG GPHVTRFKDT YFVTGIVSWG EGCARKGKYG IYTKVTAFLK
421 WIDRSMKTRG LPKAKSHAPE VITSSPLK
```

TABLE 3

Polypeptide Sequence of Factor Xa (SEQ ID NO: 3)

```
  1 ANSFLEEMKK GHLERECMEE TCSYEEAREV FEDSDKTNEF WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDSG GPHVTRFKDT YFVTGIVSWG EGCARKGKYG IYTKVTAFLK
421 WIDRSMKTRG LPKAKSHAPE VITSSPLK
```

"Native fXa" or "wild-type fXa" refers to the fXa naturally present in plasma or being isolated in its original, unmodified form, which processes the biological activity of activating prothrombin therefore promoting formation of blood clot. The term includes naturally occurring polypeptides isolated from tissue samples as well as recombinantly produced fXa. "Active fXa" refers to fXa having the biological activity of activating prothrombin. "Active fXa" may be a native fXa or modified fXa that retains procoagulant activity.

"fXa Derivatives" or "modified fXa" or "derivatives of a factor Xa protein" refers to fXa proteins that have been modified but can still bind, either directly or indirectly, to a factor Xa inhibitor.

The derivatives may have modified active sites and/or a modified Gla domain. Additional modifications are also contemplated. It is contemplated that such modifications may be made in one or more of the following ways: deletion of one or more of the amino acid from the sequence, substitution of one or more amino acid residues with one or more different amino acid residues, and/or manipulation of one or more amino acid side chains or its "C" or "N" terminals.

The term "active site" refers to the part of an enzyme or antibody where a chemical reaction occurs. A "modified active site" is an active site that has been modified structurally to provide the active site with increased or decreased chemical reactivity or specificity. It is contemplated that the active site includes not only the actual site but also a domain containing the active site. Examples of active sites include, but are not limited to, the catalytic domain of human factor X comprising the 235-488 amino acid residues, and the catalytic domain of human factor Xa comprising the 195-488 amino acid residues. The catalytic triad equivalent to H57-D102-S195 in chymotrypsin numbering are located at His236, Asp282, and Ser379. Examples of modified active site include, but are not limited to, the catalytic triad residues individually or in combination. One modification relates to a fXa derivative having a modified active site Ser379Ala. Additional examples, include modifications to the catalytic domain of human factor Xa comprising 195-448 amino acid residues with at least one amino acid substitution at position Arg306, Glu310, Arg347, Lys351, Lys414, or Arg424.

The term "factor Xa inhibitors" or "inhibitors of factor Xa" refer to compounds that can inhibit, either directly or indirectly, the coagulation factor Xa's activity of catalyzing conversion of prothrombin to thrombin in vitro and/or in vivo. Examples of known fXa inhibitors include, without limitation, edoxaban, fondaparinux, idraparinux, biotinylated idraparinux, enoxaparin, fragmin, NAP-5, rNAPc2, tissue factor pathway inhibitor, DX-9065a (as described in, e.g., Herbert, J. M., et al, *J Pharmacol Exp Ther.* 1996 276 (3): 1030-8), YM-60828 (as described in, e.g., Taniuchi, Y., et al, *Thromb Haemost.* 1998 79 (3): 543-8), YM-150 (as described in, e.g., Eriksson, B. I. et. al, *Blood* 2005; 106 (11), Abstract 1865), apixaban, rivaroxaban, PD-348292 (as described in, e.g., Pipeline Insight: Antithrombotics-Reaching the Untreated Prophylaxis Market, 2007), otamixaban, razaxaban (DPC906), BAY 59-7939 (as described in, e.g., Turpie, A. G., et al, *J. Thromb. Haemost.* 2005, 3 (11): 2479-86), edoxaban (as described in, e.g., Hylek EM, Curr Opin Invest Drugs 2007 8 (9): 778-783), LY517717 (as described in, e.g., Agnelli, G., et al, *J. Thromb. Haemost.* 2007 5 (4): 746-53), GSK913893, betrixaban and derivatives thereof. Low molecular weight heparin ("LMWH") is also considered a factor Xa inhibitor.

In one embodiment, the derivative of the invention binds, either directly or indirectly to a factor Xa inhibitor. The terms "binding," "binds," "recognition," or "recognize" as used herein are meant to include interactions between molecules that may be detected using, for example, a hybridization assay. The terms are also meant to include "binding" interactions between molecules. Interactions may be, for example, protein-protein, protein-nucleic acid, protein-small molecule or small molecule-nucleic acid in nature. Binding may be "direct" or "indirect". "Direct" binding comprises direct physical contact between molecules. "Indirect" binding between molecules comprises the molecules having direct physical contact with one or more intermediate molecules simultaneously. For example, it is contemplated that derivatives of the invention indirectly bind and substantially neutralize low molecular weight heparin and other indirect inhibitors of factor Xa. This binding can result in the formation of a "complex" comprising the interacting molecules. A "complex" refers to the binding of two or more molecules held together by covalent or non-covalent bonds, interactions or forces.

"Neutralize," "reverse" or "counteract" the activity of an inhibitor of fXa or similar phrases refer to inhibit or block the factor Xa inhibitory or anticoagulant function of a fXa inhibitor. Such phrases refer to partial inhibition or blocking of the function, as well as to inhibiting or blocking most or all of fXa inhibitor activity, in vitro and/or in vivo. These terms also refer to corrections of at least about 20% of fXa inhibitor dependent pharmacodynamic or surrogate markers. Examples of markers include, but are not limited to INR, PR, aPTT, ACT, anti-fXa units, thrombin generation (Technothrombin TGA), thromboelastogrpahy, CAT (calibrated automated thrombogram) and the like.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "equivalent thereof" when referring to a reference protein, polypeptide or nucleic acid, intends those having minimal homology while still maintaining desired functionality. It is contemplated that any modified protein mentioned herein also includes equivalents thereof. For example, the homology can be, at least 75% homology and alternatively, at least 80%, or alternatively at least 85%, or alternatively at least 90%, or alternatively at least 95%, or alternatively 98% percent homology and exhibit substantially equivalent biological activity to the reference polypeptide or protein. A polynucleotide or polynucleotide region (or a polypeptide or polypeptide region) has a certain percentage (for example, 80%, 85%, 90%, or 95%) of "sequence identity" to another sequence means that, when aligned, that percentage of bases (or amino acids) are the same in comparing the two sequences. It should be noted that when only the heavy chain of fXa (or a related serine protease) is used, the overall homology might be lower than 75%, such as, for example, 65% or 50% however, the desired functionality remains.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences.

II. Preparation of Factor Xa and Derivatives

Andexanet alfa, or simply andexanet, is a modified factor Xa polypeptide that has been approved in the U.S. and Europe for patients treated with rivaroxaban or apixaban, when reversal of anticoagulation is needed due to life-threatening or uncontrolled bleeding. Also referred to as the r-Antidote, the structure and activities of andexanet are described in U.S. Pat. No. 8,153,590.

Andexanet is a processed two-chain polypeptide processing product of SEQ ID NO:4, after cleavage of the —RKRRKR— (SEQ ID NO:7) linker. Andexanet is represented by SEQ ID NO: 5, which includes a light chain (SEQ ID NO:6) and a heavy chain (SEQ ID NO:8). The light chain and the heavy chain are connected with a single disulfide bond between Cysteine 98 (Cys98) of the light chain and Cysteine 108 (Cys108) of the heavy chain. Like the wild-type fXa, in certain production batches, Andexanet undergoes post-translational modifications resulting in glycosylation at certain amino acid residues, e.g., Ser56, Ser72, Ser76 and Thr82 of the light chain and Thr249 of the heavy chain, and a modified residue, (3R)-3-hydroxyAsp at Asp29 of the light chain. Further, in addition to the inter-chain disulfide bond, there can be intra-chain disulfide bonds formed between Cysteines 16 and 27, 21 and 36, 38 and 47, 55 and 66, 62 and 75, and 77 and 90 of the light chain, and between Cysteines 7 and 12, 27 and 43, 156 and 170, and 181 and 209 of the heavy chain.

TABLE 4

Amino acid sequence of andexanet precursor prior to removal of -RKRRKR-linker (SEQ ID NO: 4)

Light Chain Fragment (SEQ ID NO: 6)

```
  1 ANSFL                                   F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Linker (SEQ ID NO: 7)

```
  RKRRKR
```

Heavy Chain Fragment (SEQ ID NO: 8)

```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

Amino acid residue number is based on mature inactive fX (SEQ ID NO: 2)

TABLE 5

Amino acid sequence of andexanet (SEQ ID NO: 5)

Light Chain (SEQ ID NO: 6)

```
  1 ANSFL                                   F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Heavy Chain (SEQ ID NO: 8)

```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

Amino acid residue number is based on mature inactive fX (SEQ ID NO: 2)

The precursor of Andexanet, SEQ ID NO:4, contains three mutations relative to the wild type fXa. The first mutation is the deletion of 6-39 aa in the Gla-domain of fX. The second mutation is replacing the activation peptide sequence 143-194 aa with —RKR—. This produces a —RKRRKR— (SEQ ID NO:7) linker connecting the light chain and the heavy chain. Upon secretion, this linker is cleaved resulting in a two-chain polypeptide (Andexanet). The third mutation is mutation of active site residue S379 to an Ala residue.

Due to these structural changes, Andexanet does not compete with fXa in assembling into the prothrombinase complex and has reduced or no catalytic activities. Accordingly, Andexanet can sequester circulating fXa inhibitors without interfering with the native coagulation mechanisms. Similar antidotes have also been disclosed, including those that further have deletions in the EGF-1 or EGF-2 domain.

SEQ ID NO:4 is the precursor protein that is expressed in host cells to produce Andexanet, which can be digested by endogenous or a super-transfected furin protein that targets the —RKRRKR— (SEQ ID NO:7) linker. It was believed that the activation peptide (AP) from the wild-type fX is not necessary as it has been replaced by the artificial —RKRRKR— (SEQ ID NO:7) linker.

It was discovered herein, however, that inclusion of the AP can increase the expression of the processed two-chain product. Nevertheless, inclusion of the AP in the precursor proteins, such as at the N-terminus of the heavy chain, presents a challenge for manufacturing. Protein manufacturing is typically done with CHO cells, which do not possess enzymatic activity to process factor X naturally for the cleavage site -LTR— between AP and the N-terminus of the heavy chain (SEQ ID NO: 2). Therefore, the fXa derivatives include certain linkers that can be cleaved by endogenous furin in CHO cells or co-transfected with a furin protease which recognizes the —RKR— and —RKRRKR— (SEQ ID NO:7) linkers.

In this context, it was discovered that, if the AP is attached to the protein through furin-recognizable linkers (e.g., C04-C06), furin could process it too early, defeating the purpose of increasing expression. Additionally, the processed two-chain molecule might be inactive if the furin-recognizable linker was not processed properly. On the other hand, if the AP is fused to the light chain in a non-cleavable manner (e.g., C07), it did not have the ability to increase protein expression. Only when the AP was fused to the C-terminal end of the heavy chain, in a non-cleavable manner, did it have the best effect in increasing protein expression and functional activity.

Another discovery was that deletion of the 13 or even 15 C-terminal amino acid residues (Delta HC-13 and Delta HC-15, respectively) of the heavy chain did not have significant impact on the expression or activity of the protein. By contrast, deletion of 20 C-terminal amino acid residues from the C-terminus of HC (Delta HC-20) significantly reduced the expression of the protein. This was unexpected in view of the conventional wisdom as demonstrated in, e.g., Branchini et al., *Journal of Thrombosis and Haemostasis,* 13:1468-1474 (2015), that truncation of native FX up to 20 amino acids residuals did not significantly affect factor X expression. More surprisingly, the impact of C-terminal truncation on protein expressions could be rescued by fusing AP to the C-terminal of FXa and derivatives.

In accordance with one embodiment of the present disclosure, therefore, provided is a precursor protein that includes a sequence of formula (I):

*LC-L1-HC-L2-AP* (I).

Here, LC denotes a protein fragment that includes the amino acid sequence of SEQ ID NO: 13 or a biological equivalents, such as a peptide having at least 85% sequence identity to SEQ ID NO:13. HC denotes a protein fragment that includes the amino acid sequence of SEQ ID NO: 11 or a biological equivalents, such as a peptide having at least 85% sequence identity to SEQ ID NO:11. In some embodiments, L2 includes at least the first 1, 2, 3, 4, 5, 6, 7, 8, 9, or 10 amino acid residues of the beta peptide (RGLPKAKSHAPEVITSSPLK (SEQ ID NO:38)).

L1 denotes a protein linker that includes a protease recognition site. The protease, in some embodiments, may be furin. L2, on the other hand, can be null (in other words, optional) or a peptide linker. When L2 is the linker, however, L2 cannot be processed by the protease. Therefore, when the protein is incubated with the protease, the protease can digest the protein to make a two-chain polypeptide, one of which includes LC, and the other includes HC-L2-AP. In some embodiments, the produced two-chain polypeptide is capable of binding to a factor Xa inhibitor.

Interestingly, in a first set of experiments, the expression-enhancing effect of AP was not observed with human serum albumin (HSA), a protein commonly used to enhance expression or stability of expressed proteins. See C10 in Example 2. However, in a further experiment (Example 3), two precursor constructs with the HSA fused to the N-terminus of the light chain, C13 and C14 exhibited greatly improved expression and activities. Accordingly, it is contemplated that the full deletion of the Gla domain (C10 had partial deletion of the Gla domain) enhanced the effect of HSA. In other words, the expression-enhancing effect of HSA was more pronounced when the HSA was fused to the EGF1 domain directly.

In accordance with another embodiment of the present disclosure, therefore, provided is a precursor protein that includes a sequence of formula (II):

*HSA-L2-LC-L1-HC* (II).

In another embodiment, also provided is a precursor protein that includes a sequence of formula (III):

*LC-L1-HC-L2-HSA* (III).

Here, HSA denotes a human serum albumin (HSA) or a variant having at least 85% sequence identity to the HSA; L1 is a peptide linker comprising a protease recognition site; L2 is absent or is a peptide linker that cannot be processed by the protease; LC comprises the amino acid sequence of SEQ ID NO:13 or a peptide having at least 85% sequence identity to SEQ ID NO: 13; and HC comprises the amino acid sequence of SEQ ID NO:11 or a peptide having at least 85% sequence identity to SEQ ID NO:11. The protein of formula (II), when the L1 is processed by the protease, produce a two-chain polypeptide comprising the LC and HC on separate chains, wherein the two-chain polypeptide is capable of binding to a factor Xa inhibitor. In some embodiments, the LC does not include amino acid residues 1-45 of SEQ ID NO:2. In some embodiments, L2 is absent.

In some embodiments, the protein of formula (I) can further include a HSA fused to the N-terminal end of the light chain, or the C-terminal end of the heavy chain. In some embodiments, the protein of formula (II) can further include an AP fused to the C-terminal end of the heavy chain. In some embodiments, the protein of formula (III) can further include an AP fused to the N-terminal end of the light chain.

In some embodiments, any protein of the present disclosure can be fused to an Fc fragment of an immunoglobulin. The fragment crystallizable region (Fc region) is the tail region of an antibody that interacts with cell surface receptors called Fc receptors and some proteins of the complement system. In IgG, IgA and IgD antibody isotypes, the Fc region is composed of two identical protein fragments, derived from the second and third constant domains of the antibody's two heavy chains.

In some embodiments, the Fc fragment used is an IgG, such as IgG1, IgG2 or IgG4, Fc fragment. In some embodiments, the Fc fragment further includes, besides the CH2 and CH3 regions, the CH1 region. An example Fc fragment sequence is provided in Table 24, SEQ ID NO: 46. In some embodiments, the fusion protein includes a signal peptide, such as SEQ ID NO: 34-36 or 45.

In some embodiments, only one chain of the Fc fragment is fused to the fXa derivative. In some embodiments, both chains of the Fc fragment are fused to the fXa derivative.

The term "furin" or "paired basic amino acid cleaving enzyme," as used herein, refers to a protein having an amino acid sequence substantially identical to any of the representative Furin sequences of GenBank Accession Nos. NP_002560 (human), NP_001074923 (mouse) or NP_062204 (rat). Suitable cDNA encoding furin are provided at GenBank Accession Nos. NM_002569 (human), NM_001081454 (mouse) or NM_019331 (rat). In a particular aspect, furin refers to a human furin.

Human serum albumin (HSA) is the serum albumin found in human blood. HSA constitutes about half of serum protein. It is produced in the liver and is soluble in water. Albumin transports hormones, fatty acids, and other compounds, buffers pH, and maintains oncotic pressure, among other functions. Albumin is synthesized in the liver as preproalbumin, which has an N-terminal peptide that is removed before the nascent protein is released from the rough endoplasmic reticulum. The product, proalbumin, is in turn cleaved in the Golgi vesicles to produce the secreted albumin. The HSA can have the native sequence or with a single Cys34Ser mutation (SEQ ID NO:15) to remove the free cysteine in native HSA, as tested herein.

AP denotes a protein fragment that includes an activation peptide. An "activation peptide" is peptide that is attached, either covalently or non-covalently, to a protein and maintains that protein inactive until the activation peptide is removed. In some embodiments, the activation peptide includes four or more glycosylation sites. It is known that amino acid residues such as Asp, Ser, Tyr, and Thr are suitable glycosylation sites. In some embodiments, the AP is from 10 to 100 amino acid residues long (or alternatively from 10 to 80, from 15 to 70, from 20 to 60, or from 10 to 50 amino acid residues long) and includes 1, 2, 3, 4, 5, 6, 7, 8, 9, 10, 11, 12, 13, 14, 15, 16, 17, 18, 19, or 20 glycosylation sites.

Activation peptides exist in wild-type proteins, such as the precursors of factor IX (fIX), factor X (fX), factor XIII (fXIIII), factor II (prothrombin) and protein C. Their respective sequences are listed in Table 6.

TABLE 6

Example activation peptides

Activation peptide of factor X (SEQ ID NO: 12)

SVAQATSSSG EAPDSITWKP YDAADLDPTE NPFDLLDFNQ

TQPERGDNNL TR

Activation peptide of factor IX (SEQ ID NO: 31)

AETVFPDVDY VNSTEAETIL DNITQSTQSF NDFTR

Activation peptide of factor XIII
(SEQ ID NO: 32)

MSETSRTAFG GRRAVPPNNS NAAEDDLPTV ELQGVVPR

Activation peptide of Protein C (SEQ ID NO: 33)

DTEDQEDQVD PR

Activation peptide of factor II, AP1
(SEQ ID NO: 39)

ANTFLEEVRK GNLERECVEE TCSYEEAFEA LESSTATDVF

WAKYTACETA RTPRDKLAAC LEGNCAEGLG TNYRGHVNIT

RSGIECQLWR SRYPHKPEIN STTHPGADLQ ENFCRNPDSS

TTGPWCYTTD PTVRRQECSI PVCGQDQVTV AMTPR

Activation peptide of factor II, AP2
(SEQ ID NO: 40)

SEGSSVNLSP PLEQCVPDRG QQYQGRLAVT THGLPCLAWA

SAQAKALSKH QDFNSAVQLV ENFCRNPDGD EEGVWCYVAG

KPGDFGYCDL NYCEEAVEEE TGDGLDEDSD RAIEGRTATS

EYQTFFNPR

In some embodiments, the activation peptide includes the amino acid sequence of SEQ ID NO: 12, 31, 32, 33, 39 or 40, or include an amino acid sequence having at least 85% sequence identity to SEQ ID NO:12, 31, 32, 33, 39 or 40. In some embodiments, the activation peptide includes an amino acid sequence having at least 85%, or alternatively at least 70%, 75%, 80%, 90%, 95%, 98% or 99%, sequence identity to SEQ ID NO:12. In some embodiments, the activation peptide includes an amino acid sequence derived from SEQ ID NO:12 with one, two or three amino acid addition, deletions and/or substitutions. In some embodiments, the activation peptide includes an amino acid sequence having at least 85%, or alternatively at least 70%, 75%, 80%, 90%, 95%, 98% or 99%, sequence identity to SEQ ID NO:31. In some embodiments, the activation peptide includes an amino acid sequence derived from SEQ ID NO:31 with one, two or three amino acid addition, deletions and/or substitutions. In some embodiments, the activation peptide includes an amino acid sequence having at least 85%, or alternatively at least 70%, 75%, 80%, 90%, 95%, 98% or 99%, sequence identity to SEQ ID NO:32. In some embodiments, the activation peptide includes an amino acid sequence derived from SEQ ID NO:32 with one, two or three amino acid addition, deletions and/or substitutions. In some embodiments, the activation peptide includes an amino acid sequence having at least 85%, or alternatively at least 70%, 75%, 80%, 90%, 95%, 98% or 99%, sequence identity to SEQ ID NO:33. In some embodiments, the activation peptide includes an amino acid sequence derived from SEQ ID NO:33 with one, two or three amino acid addition, deletions and/or substitutions. In some embodiments, the activation peptide includes an amino acid sequence having at least 85%, or alternatively at least 70%, 75%, 80%, 90%, 95%, 98% or 99%, sequence identity to SEQ ID NO:39. In some embodiments, the activation peptide includes an amino acid sequence derived from SEQ ID NO:39 with one, two or three amino acid addition, deletions and/or substitutions. In some embodiments, the activation peptide includes an amino acid sequence having at least 85%, or alternatively at least 70%, 75%, 80%, 90%, 95%, 98% or 99%, sequence identity to SEQ ID NO:40. In some embodiments, the activation peptide includes an amino acid sequence derived from SEQ ID NO:40 with one, two or three amino acid addition, deletions and/or substitutions. In some embodiments, the activation peptide is from 10 to 100 amino acid residues long (or alternatively from 10 to 80, from 15 to 70, from 20 to 60, or from 10 to 50 amino acid residues long) and includes 1, 2, 3, 4, 5, 6, 7, 8, 9, 10, 11, 12, 13, 14, 15, 16, 17, 18, 19, or 20 glycosylation sites.

In some embodiments, the protease is furin, but other proteases are also within the scope of the present disclosure, for example, other proprotein convertases such as PC5 or coagulation enzymes such as FXa and thrombin. Examples of peptide linkers suitable for furin include —RKR— and —RKRRKR— (SEQ ID NO:7).

As provided, in some embodiments, L2 is absent (null). In some embodiments, L2 is peptide linker of 1-50 (or 1-40, 1-30, 1-25, 1-20, 5-40, 10-30, 15-35) amino acid residues in length. The peptide linker if preferably flexible, such as those having at least 30%, 40%, 50%, 60%, 70%, 80% or 90% Gly and/or Ser.

The produced two-chain polypeptide, in some embodiment, is suitable to be used as an antidote to factor fXa inhibitor-based anticoagulant treatments. In some embodiments, the two-chain polypeptide cannot compete with fXa in assembling into the prothrombinase complex, has reduced capacity to assemble into a prothrombin complex, or cannot assemble into a prothrombin complex. Assembly into the prothrombin complex requires a functional Gla domain. In some embodiments, the LC does not include a substantial portion of the Gla domain, such as does not include amino acids 6-39 of SEQ ID NO:2. In some embodiments, the LC does not include amino acids 1-45 of SEQ ID NO:2.

In some embodiments, the LC includes the amino acid sequence of SEQ ID NO:6 or includes an amino acid sequence having at least 85%, or alternatively at least 70%, 75%, 80%, 90%, 95%, 98% or 99%, sequence identity to SEQ ID NO:6.

In some embodiments, the LC includes the full light chain sequence of the wild-type fXa (i.e., amino acid residues 1-139 of SEQ ID NO:3), or an amino acid sequence having at least 85%, or alternatively at least 70%, 75%, 80%, 90%, 95%, 98% or 99%, sequence identity to the full length light chain sequence of the wild-type fXa.

The produced two-chain polypeptide, in some embodiments, has reduced catalytic activity as compared to a wild-type human factor Xa. This can be achieved, for instance, by mutation of one or more of the active sites in the heavy chain, e.g., His236, Asp282, and Ser379 (amino acids 236, 282 and 379 of SEQ ID NO:2).

In some embodiments, the HC includes at least the amino acid sequence of SEQ ID NO: 10 or an amino acid sequence having at least 85%, or alternatively at least 70%, 75%, 80%, 90%, 95%, 98% or 99%, sequence identity to SEQ ID NO:10. In some embodiments, the HC includes at least the amino acid sequence of SEQ ID NO:11 or an amino acid sequence having at least 85%, or alternatively at least 70%, 75%, 80%, 90%, 95%, 98% or 99%, sequence identity to SEQ ID NO:11. In some embodiments, the HC includes the amino acid sequence of SEQ ID NO: 7 or an amino acid sequence having at least 85%, or alternatively at least 70%, 75%, 80%, 90%, 95%, 98% or 99%, sequence identity to SEQ ID NO:7.

In some embodiments, the HC includes the full heavy chain sequence of the wild-type fXa (i.e., amino acid residues 140-393 of SEQ ID NO:3), or an amino acid sequence having at least 85%, or alternatively at least 70%, 75%, 80%, 90%, 95%, 98% or 99%, sequence identity to the full length heavy chain sequence of the wild-type fXa.

In some embodiments, the protein (or the HC) does not include the 13 C-terminal amino acid residues (436-448 of SEQ ID NO:2) of the heavy chain. In some embodiments, the protein (or the HC) does not include the 15 C-terminal amino acid residues (434-448 of SEQ ID NO:2) of the heavy chain.

Non-limiting examples of the protein sequences include SEQ ID NO:25 and 26.

In some embodiments, a signal peptide (or in combination with pro-peptide) is included at the N-terminal end of the protein. Example signal/pro-peptides are listed in Table 7.

TABLE 7

| Signal or signal/pro-peptides |
|---|
| Human fX signal peptide (SEQ ID NO: 34) |
| MGRPLHLVLL SASLAGLLLL GESLFIRREQ ANNILARVTR |
| Human prothrombin signal peptide (SEQ ID NO: 35) |
| MAHVRGLQLP GCLALAALCS LVHS |
| Human transferrin signal peptide (SEQ ID NO: 36) |
| MRLAVGALLV CAVLGLCLA |
| Prothrombin signal/pro-peptide (SEQ ID NO: 37) |
| MAHVRGLQLP GCLALAALCS LVHSQHVFLA PQQARSLLQR VRR |
| Ig kappa LC signal peptide (SEQ ID NO: 45) |
| METDTLLLWV LLLWVPGSTG |

The disclosed precursor protein can have the same amino acid residues as the wild-type fX, except for the indicated deletions. In a preferred embodiment, certain amino acid substitutions are introduced, such as the Ser379Ala substitution as shown in SEQ ID NO:4, leading to production of an effective antidote to fXa inhibitors. In some embodiments, the precursor protein is capable of, when the L1 and L2 are digested, producing a two-chain polypeptide capable of binding to a factor Xa inhibitor. When amino acid substitutions are introduced, in some embodiments, the digested two-chain polypeptide cannot compete with fXa in assembling into the prothrombinase complex, has reduced capacity to assemble into a prothrombin complex, or cannot assemble into a prothrombinase complex, and/or has reduced catalytic activity as compared to a wild-type human factor Xa.

Also provided, in some embodiments, are two-chain polypeptides that can be obtained by processing the precursor protein of the present disclosure. In one embodiment, provided is a two-chain polypeptide comprising a light chain that comprises the amino acid sequence of SEQ ID NO: 13 or a peptide having at least 85% sequence identity to SEQ ID NO:13, and a heavy chain that comprises a first fragment comprising the amino acid sequence of SEQ ID NO:11 or a peptide having at least 85% sequence identity to SEQ ID NO:11, and a second fragment that is at the C-terminal side of the first fragment and comprises an activation peptide, wherein the two-chain polypeptide is capable of binding to a factor Xa inhibitor. Examples of such two-chain polypeptides are provided in Tables 8 and 9 below.

TABLE 8

| Amino acid sequence of activated product of construct C08 (SEQ ID NO: 29) |
|---|
| Light Chain (SEQ ID NO: 13) |
| 1 DGDQC ETSPCQNQGK |
| 61 CKDGLGEYTC TCLEGFEGKN CELFTRKLCS LDNGDCDQFC HEEQNSVVCS CARGYTLADN |
| 121 GKACIPTGPY PCGKQTLER |

TABLE 8-continued

Amino acid sequence of activated product of
construct C08 (SEQ ID NO: 29)

Heavy Chain (SEQ ID NO: 16)
HC Portion (SEQ ID NO: 11)

181           IVGGQE CKDGECPWQA LLINEENEGF CGGTILSEFY ILTAAHCLYQ

241 AKRFKVRVGD RNTEQEEGGE AVHEVEVVIK HNRFTKETYD FDIAVLRLKT PITFRMNVAP

301 ACLPERDWAE STLMTQKTGI VSGFGRTHEK GRQSTRLKML EVPYVDRNSC KLSSSFIITQ

361 NMFCAGYDTK QEDACQGDAG GPHVTRFKDT YFVTGIVSWG EGCARKGKYG IYTKVTAFLK

421 WIDRSMKTRG LPK

AP Portion (SEQ ID NO: 12)

121                  SVAQATSS SGEAPDSITW KPYDAADLDP TENPFDLLDF

181 NQTQPERGDN NLTR

Amino acid residue number is based on mature inactive fX (SEQ ID NO: 2)

TABLE 9

Amino acid sequence of activated product of
construct C09 (SEQ ID NO: 30)

Light Chain (SEQ ID NO: 13)

1                                          DGDQC ETSPCQNQGK

61 CKDGLGEYTC TCLEGFEGKN CELFTRKLCS LDNGDCDQFC HEEQNSVVCS CARGYTLADN

121 GKACIPTGPY PCGKQTLER

Heavy Chain (SEQ ID NO: 17)
HC Portion (SEQ ID NO: 11)

181           IVGGQE CKDGECPWQA LLINEENEGF CGGTILSEFY ILTAAHCLYQ

241 AKRFKVRVGD RNTEQEEGGE AVHEVEVVIK HNRFTKETYD FDIAVLRLKT PITFRMNVAP

301 ACLPERDWAE STLMTQKTGI VSGFGRTHEK GRQSTRLKML EVPYVDRNSC KLSSSFIITQ

361 NMFCAGYDTK QEDACQGDAG GPHVTRFKDT YFVTGIVSWG EGCARKGKYG IYTKVTAFLK

421 WIDRSMKTRG LPK

Linker (SEQ ID NO: 14)

SSGGSGGSGG SGGSGGSGGS GGSGGSGGSG S

AP Portion (SEQ ID NO: 12)

121                  SVAQATSS SGEAPDSITW KPYDAADLDP TENPFDLLDF

181 NQTQPERGDN NLTR

Amino acid residue number is based on mature inactive fX (SEQ ID NO: 2)

Polynucleotides and Host Cells

This disclosure also provides polynucleotides encoding the disclosed proteins, and host cells containing one or more of the polypeptides. In one aspect, the polypeptides are expressed and present on the cell surface (extracellularly). Suitable cells containing the inventive polypeptides include prokaryotic and eukaryotic cells, which include, but are not limited to bacterial cells, yeast cells, insect cells, animal cells, mammalian cells, murine cells, rat cells, sheep cells, simian cells and human cells. Examples of bacterial cells include *Escherichia coli, Salmonella enterica* and *Streptococcus gordonii*. The cells can be purchased from a commercial vendor such as the American Type Culture Collection (ATCC, Rockville Maryland, USA) or cultured from an isolate using methods known in the art. Examples of suitable eukaryotic cells include, but are not limited to 293T HEK cells, as well as the hamster cell line CHO, BHK-21; the murine cell lines designated NIH3T3, NSO, C127, the simian cell lines COS, Vero; and the human cell lines HeLa, PER.C6 (commercially available from Crucell) U-937 and Hep G2. A non-limiting example of insect cells include *Spodoptera frugiperda*. Examples of yeast useful for expression include, but are not limited to *Saccharomyces, Schizosaccharomyces, Hansenula, Candida, Torulopsis, Yarrowia*, or *Pichia*. See e.g., U.S. Pat. Nos. 4,812,405; 4,818,700; 4,929,555; 5,736,383; 5,955,349; 5,888,768 and 6,258,559.

In some embodiments, the host cell is further transfected with a polynucleotide that encodes a furin protein.

In addition to species specificity, the cells can be of any particular tissue type such as neuronal or alternatively a somatic or embryonic stem cell such as a stem cell that can or cannot differentiate into a neuronal cell, e.g., embryonic stem cell, adipose stem cell, neuronal stem cell and hematopoietic stem cell. The stem cell can be of human or animal origin, such as mammalian.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Example 1. Preparation of Expression Vectors

This example generated polynucleotide constructs coding for precursor proteins that can be used to produce factor Xa derivatives, including Andexanet, which can be used to neutralize factor Xa inhibitors. The precursor protein sequences are listed in Tables 10-20 and illustrated in FIG. 1, referred to as C01-C11.

Compared to the precursor (SEQ ID NO:4) of Andexanet, C01 (SEQ ID NO:18) contained a deletion of 20 C-terminal amino acid residues of the heavy chain. Similarly, C02 (SEQ ID NO:19) and C03 (SEQ ID NO:20) contained a deletion of the 13 and 15 C-terminal amino acid residues, respectively.

On the basis of C03, the factor Xa activation peptide (AP) was added back in precursor C04 (SEQ ID NO:21). Different from the wild-type fX, a —RKRRKR— (SEQ ID NO:7) linker was placed between the AP and the heavy chain to facilitate processing by furin (there was also a —RKR— linker between the light chain and the AP, as in the wild type fX). Another version of this precursor, C05 (SEQ ID NO:22), which did not have the C-terminal truncation but removed the N-terminal 11 amino acids of the light chain, was also prepared. Yet another precursor, C06 (SEQ ID NO:23) contained both the N-terminal 11-amino acid truncation and the C-terminal 15-amino acid truncation, was also prepared. In C07 (SEQ ID NO:24), the natural —RKR— linker was removed between the light chain and the AP In precursors C08 (SEQ ID NO:25) and C09 (SEQ ID NO:26), the AP was placed at the C-terminal side of the heavy chain. The AP was immediately fused to the heavy chain in C08 and was fused through an artificial linker (-KSS(GSS)$_g$GSS— (SEQ ID NO:14)) in C09.

In precursors C10 (SEQ ID NO:27) and C11 (SEQ ID NO:28), a human serum albumin (HSA, SEQ ID NO:15) was fused to either the N-terminus or the C-terminus, where HSA can have the native sequence or with a single Cys34Ser mutation (SEQ ID NO:15) to remove the free cysteine in native HSA. In C10, the heavy chain was intact and in C11, the heavy chain had a 15-amino acid truncation at the C-terminus.

TABLE 10

Amino acid sequence of construct C01 (SEQ ID NO: 18)

Light Chain Fragment (SEQ ID NO: 6)

```
  1 ANSFL                              F WNKYKDGDQC ETSPCQNQGK

61 CKDGLGEYTC TCLEGFEGKN CELFTRKLCS LDNGDCDQFC HEEQNSVVCS CARGYTLADN

121 GKACIPTGPY PCGKQTLER
```

Linker (SEQ ID NO: 7)

```
    RKRRKR
```

Heavy Chain Fragment truncated-20 (SEQ ID NO: 9)

```
181               IVGGQE CKDGECPWQA LLINEENEGF CGGTILSEFY ILTAAHCLYQ

241 AKRFKVRVGD RNTEQEEGGE AVHEVEVVIK HNRFTKETYD FDIAVLRLKT PITFRMNVAP

301 ACLPERDWAE STLMTQKTGI VSGFGRTHEK GRQSTRLKML EVPYVDRNSC KLSSSFIITQ

361 NMFCAGYDTK QEDACQGDAG GPHVTRFKDT YFVTGIVSWG EGCARKGKYG IYTKVTAFLK

421 WIDRSMKT
```

Amino acid residue number is based on mature inactive fX (SEQ ID NO: 2)

TABLE 11

Amino acid sequence of construct C02 (SEQ ID NO: 19)

Light Chain Fragment (SEQ ID NO: 6)

```
  1 ANSFL                                    F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Linker (SEQ ID NO: 7)

```
    RKRRKR
```

Heavy Chain Fragment truncated-13 (SEQ ID NO: 10)

```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAK
```

Amino acid residue number is based on mature inactive fX (SEQ ID NO: 2)

25

TABLE 12

Amino acid sequence of construct C03 (SEQ ID NO: 20)

Light Chain Fragment (SEQ ID NO: 6)

```
  1 ANSFL                                    F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Linker (SEQ ID NO: 7)

```
    RKRRKR
```

Heavy Chain Fragment truncated-15 (SEQ ID NO: 11)

```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPK
```

Amino acid residue number is based on mature inactive fX (SEQ ID NO: 2)

TABLE 13

Amino acid sequence of construct C04 (SEQ ID NO: 21)

Light Chain Fragment (SEQ ID NO: 6)

```
  1 ANSFL                                    F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

TABLE 13-continued

| Amino acid sequence of construct C04 (SEQ ID NO: 21) |
|---|

Linker

```
121              R KR
```

Activation Peptide (SEQ ID NO: 12)

```
121                SVAQATSS SGEAPDSITW KPYDAADLDP TENPFDLLDF
181 NQTQPERGDN NLTR
```

Linker (SEQ ID NO: 7)

```
RKRRKR
```

Heavy Chain Fragment truncated-15 (SEQ ID NO: 11)

```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPK
```

Amino acid residue number is based on mature inactive fX (SEQ ID NO: 2)

TABLE 14

| Amino acid sequence of construct C05 (SEQ ID NO: 22) |
|---|

Light Chain Fragment truncated (SEQ ID NO: 13)

```
  1                                         DGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Linker

```
121              R KR
```

Activation Peptide (SEQ ID NO: 12)

```
121                SVAQATSS SGEAPDSITW KPYDAADLDP TENPFDLLDF
181 NQTQPERGDN NLTR
```

Linker (SEQ ID NO: 7)

```
    RKRRKR
```

Heavy Chain Fragment (SEQ ID NO: 8)

```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

Amino acid residue number is based on mature inactive fX (SEQ ID NO: 2)

TABLE 15

Amino acid sequence of construct C06 (SEQ ID NO: 23)

Light Chain Fragment truncated (SEQ ID NO: 13)

```
  1                                              DGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Linker

```
121            R KR
```

Activation Peptide (SEQ ID NO: 12)

```
121                   SVAQATSS SGEAPDSITW KPYDAADLDP TENPFDLLDF
181 NQTQPERGDN NLTR
```

Linker (SEQ ID NO: 7)

```
    RKRRKR
```

Heavy Chain Fragment truncated-15 (SEQ ID NO: 11)

```
181               IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPK
```

Amino acid residue number is based on mature inactive fX (SEQ ID NO: 2)

TABLE 16

Amino acid sequence of construct C07 (SEQ ID NO: 24)

Light Chain Fragment (SEQ ID NO: 13)

```
  1                                              DGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Activation Peptide (SEQ ID NO: 12)

```
121                   SVAQATSS SGEAPDSITW KPYDAADLDP TENPFDLLDF
181 NQTQPERGDN NLTR
```

Linker (SEQ ID NO: 7)

```
    RKRRKR
```

Heavy Chain Fragment truncated-15 (SEQ ID NO: 11)

```
181               IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPK
```

Amino acid residue number is based on mature inactive fX (SEQ ID NO: 2)

TABLE 17

Amino acid sequence of construct C08 (SEQ ID NO: 25)

Light Chain Fragment (SEQ ID NO: 13)

```
  1                                              DGDQC ETSPCQNGK
 61 CKDGLGEYTC TCLEGFEGKN CELFTRKLCS LDNGDCDQFC HEEQNSVVCS CARGYTLADN
121 GKACIPTGPY PCGKQTLER
```

Linker (SEQ ID NO: 7)

```
    RKRRKR
```

Heavy Chain Fragment truncated-15 (SEQ ID NO: 11)

```
181              IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPK
```

Activation Peptide (SEQ ID NO: 12)

```
121 SVAQATSS SGEAPDSITW KPYDAADLDP TENPFDLLDF
181 NQTQPERGDN NLTR
```

Amino acid residue number is based on mature inactive fX (SEQ ID NO: 2)

TABLE 18

Amino acid sequence of construct C09 (SEQ ID NO: 26)

Light Chain Fragment truncated (SEQ ID NO: 13)

```
  1                                              DGDQC ETSPCQNGK
 61 CKDGLGEYTC TCLEGFEGKN CELFTRKLCS LDNGDCDQFC HEEQNSVVCS CARGYTLADN
121 GKACIPTGPY PCGKQTLER
```

Linker (SEQ ID NO: 7)

```
    RKRRKR
```

Heavy Chain Fragment truncated-15 (SEQ ID NO: 11)

```
181              IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPK
```

Linker (SEQ ID NO: 14)

```
    SSGGSGGSGG SGGSGGSGGS GGSGGSGGSG S
```

Activation Peptide (SEQ ID NO: 12)

```
121 SVAQATSS SGEAPDSITW KPYDAADLDP TENPFDLLDF
181 NQTQPERGDN NLTR
```

Amino acid residue number is based on mature inactive fX (SEQ ID NO: 2)

TABLE 19

Amino acid sequence of construct C10 (SEQ ID NO: 27)

HSA (Human serum albumin, SEQ ID NO: 15)

DAHKSEVAHR FKDLGEENFK ALVLIAFAQY LQQSPFEDHV KLVNEVTEFA KTCVADESAE
NCDKSLHTLF GDKLCTVATL RETYGEMADC CAKQEPERNE CFLQHKDDNP NLPRLVRPEV
DVMCTAFHDN EETFLKKYLY EIARRHPYFY APELLFFAKR YKAAFTECCQ AADKAACLLP
KLDELRDEGK ASSAKQRLKC ASLQKFGERA FKAWAVARLS QRFPKAEFAE VSKLVTDLTK
VHTECCHGDL LECADDRADL AKYICENQDS ISSKLKECCE KPLLEKSHCI AEVENDEMPA
DLPSLAADFV ESKDVCKNYA EAKDVFLGMF LYEYARRHPD YSVVLLLRLA KTYETTLEKC
CAAADPHECY AKVFDEFKPL VEEPQNLIKQ NCELFEQLGE YKFQNALLVR YTKKVPQVST
PTLVEVSRNL GKVGSKCCKH PEAKRMPCAE DYLSVVLNQL CVLHEKTPVS DRVTKCCTES
LVNRRPCFSA LEVDETYVPK EFNAETFTFH ADICTLSEKE RQIKKQTALV ELVKHKPKAT
KEQLKAVMDD FAAFVEKCCK ADDKETCFAE EGKKLVAASQ AALGL

Light Chain Fragment (SEQ ID NO: 6)

```
  1 ANSFL                F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Linker (SEQ ID NO: 7)

RKRRKR

Heavy Chain Fragment (SEQ ID NO: 8)

```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

Amino acid residue number is based on mature inactive fX (SEQ ID NO: 2)

TABLE 20

Amino acid sequence of construct C11 (SEQ ID NO: 28)

Light Chain (SEQ ID NO: 6)

```
  1 ANSFL                F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Linker (SEQ ID NO: 7)

RKRRKR

Heavy Chain Fragment truncated-15 (SEQ ID NO: 11)

```
181            IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPK
```

TABLE 20-continued

Amino acid sequence of construct C11 (SEQ ID NO: 28)

HSA (Human serum albumin, SEQ ID NO: 15)

```
DAHKSEVAHR FKDLGEENFK ALVLIAFAQY LQQSPFEDHV KLVNEVTEFA KTCVADESAE

NCDKSLHTLF GDKLCTVATL RETYGEMADC CAKQEPERNE CFLQHKDDNP NLPRLVRPEV

DVMCTAFHDN EETFLKKYLY EIARRHPYFY APELLFFAKR YKAAFTECCQ AADKAACLLP

KLDELRDEGK ASSAKQRLKC ASLQKFGERA FKAWAVARLS QRFPKAEFAE VSKLVTDLTK

VHTECCHGDL LECADDRADL AKYICENQDS ISSKLKECCE KPLLEKSHCI AEVENDEMPA

DLPSLAADFV ESKDVCKNYA EAKDVFLGMF LYEYARRHPD YSVVLLLRLA KTYETTLEKC

CAAADPHECY AKVFDEFKPL VEEPQNLIKQ NCELFEQLGE YKFQNALLVR YTKKVPQVST

PTLVEVSRNL GKVGSKCCKH PEAKRMPCAE DYLSVVLNQL CVLHEKTPVS DRVTKCCTES

LVNRRPCFSA LEVDETYVPK EFNAETFTFH ADICTLSEKE RQIKKQTALV ELVKHKPKAT

KEQLKAVMDD FAAFVEKCCK ADDKETCFAE EGKKLVAASQ AALGL
```

Amino acid residue number is based on mature inactive fX (SEQ ID NO: 2)

Polynucleotides coding for these precursor proteins (with suitable signal peptides) were synthesized de novo. Following verification of these polynucleotides sequences, they were ligated into an expression vector suitable for transfection to a mammalian host cell. An example expression vector was the AB1 vector. Another expression vector used was the pcDNA3.3 vector (Thermo Fisher Scientific).

The expression vectors were transfected into host cells CHO-DUXB11, CHO-S (Thermo Fisher Scientific), ExpiCHO-S (Thermo Fisher Scientific), DG44 (Thermo Fisher Scientific), or CHO-M. The transfection was carried out using the ExpiFectamine™ CHO transfection kit (Thermo Fisher Scientific) or electroporation with reagents and electroporator (Maxcyte) according to the manufacture's recommendations.

The transfected CHO cells were cultured in shake flasks and monitored for protein expressions over time. The protein expressions were monitored transiently without prior use of antibiotics for stable cells selection. Protein expressions were also monitored using stable CHO cell pools. Stable pools were expanded and cell banks were prepared and stored in liquid nitrogen. Protein expressions with stable pools were cultured similarly as for transient expression by thawing a vial of the cell bank.

To improve the process of the linker connecting the heavy and light chains of the fXa derivatives, a second polynucleotide sequence encoding human furin protein was co-transfected in certain samples. The furin construct was introduced using a separate vector. For stable cell production, stable cell pools were first selected using pcDNA3.3 with the fXa derivatives and G-418 (0-1500 µg/mL) to generate stable pools (parental pools). The parental pools were further transfected with a second vector with furin (super-transfection). The super-transfected pools were further selected using antibiotics and prepare for cell banks.

The protein expression levels in cell culture were measured by ELISA (FX-EIA, Enzyme Research Laboratories) and characterized by western blots using monoclonal antibodies against FX/FXa heavy and light chains. Andexanet was used to construct the standard curve. Proteins in harvested cell culture fluids were purified by an affinity-based method using STI-resin to capture functional proteins.

Example 2. Testing of Expression Levels and Activities

This example tested the expression levels and activities of the fXa derivatives prepared in Example 1.

The expression and functional activities of Andexanet (AnXa) precursor (SEQ ID NO:4) and C01-C03 were tested in transient transfections (co-transfection with furin). Conditions included, chemical transfection with Expifectamine, followed by addition of enhancer and feed after 24 hrs, at 37° C., with 8% $CO_2$, 135 rpm. The results are shown in the table below.

| Construct | Day post transfection | N number | ELISA (µg/mL) | Functional activity (µg/mL) |
|---|---|---|---|---|
| AnXa precursor | 6 | 11 | 4.6 ± 1.6 | 3.8 |
| C01 | 6 | 3 | 2.6 ± 0.8 | BLQ* |
| C02 | 6 | 2 | 4.9 ± 2 | 5.9 |
| C03 | 6 | 2 | 4.1 ± 0.9 | 3.1 |

*BLQ: below level of quantification

Stable pools of these constructs were generated. The total cell culture volume was 30 mL. The cells were passaged every 3 days up to full recovery of cells at >97% viability. Conditions for titer were as follows: 32° C., 5% $CO_2$, 135 rpm; addition of feed on Day 1, 4, 7, 10. The results are shown in the table below.

| Construct | Day post transfection | N number | ELISA (µg/mL) | Functional activity (µg/mL) |
|---|---|---|---|---|
| AnXa precursor | 10 | 1 | 22.3 | 18.5 |
| C01 | 10 | 1 | 5.7 | 3.0 |
| C02 | 10 | 1 | 38.5 | 26 |
| C03 | 10 | 1 | 19.1 | 16.0 |

The following table shows the testing results when the cells were further transfected with furin.

| Construct | Day post transfection | N number | ELISA (μg/mL) | Functional activity (μg/mL) |
|---|---|---|---|---|
| AnXa precursor | 10 | 1 | 27.3 | 13 |
| C01 | 10 | 1 | 3.3 | BLQ* |
| C02 | 10 | 1 | 12.2 | 12.2 |
| C03 | 10 | 1 | 19.1 | 13.2 |

*BLQ: below level of quantification

The results showed that, in both transient and stable expression, C01 had low levels of expression, while C02 and C03 performed similarly to the Andexanet precursor. Therefore, truncation of 13 or 15 C-terminal residues from the heavy chain did not impact the protein expression or activity, but deletion of the 20-terminal residues had significant negative impact.

Compared to C01-C03, C04-C11 further included a factor X activation peptide (AP) or a human serum albumin (HSA). The AP is removed when the wild-type factor X is activated. In the production of Andexanet, the AP was not part of the construct. As shown in the results below, inclusion of the AP significantly increased protein expression. Further, when the AP was fused to the C-terminal end of the heavy chain (as opposed to the light chain), the construct yielded products that were most functionally active (C08 and C09). Fusion to the HSA was also helpful in increasing the expression and activity, but the impact was less pronounced as compared to AP.

Expression Level Measured by ELISA

| | C04 | C05 | C06 | C07 | C08 | C09 | C10 | C11 |
|---|---|---|---|---|---|---|---|---|
| Day 1 | 4.1 | 6.2 | 1.0 | 3.1 | 3.0 | 2.5 | 1.4 | 1.3 |
| Day 2 | 11.9 | 34.5 | 5.7 | 10.3 | 18.1 | 11.8 | 8.1 | 6.8 |
| Day 3 | 38.1 | 49.3 | 11.7 | 20.4 | 43.3 | 31.1 | 12.5 | 11.7 |
| Day 4 | 29.6 | 76.6 | 15.3 | 23.7 | 50.5 | 34.8 | 17.9 | 15.0 |
| Day 5 | 34.7 | 117.4 | 18.3 | 40.5 | 59.1 | 48.4 | 24.3 | 17.6 |
| Day 6 | 36.4 | 163.0 | 23.4 | 45.0 | 78.8 | 57.7 | 37.3 | 22.2 |
| Day 7 | 36.1 | 172.8 | 19.8 | 49.6 | 83.9 | 61.0 | 36.6 | 22.4 |
| Day 8 | 34.1 | 183.7 | 20.3 | 52.1 | 104.0 | 65.2 | 41.2 | 26.1 |
| Day 9 | 32.9 | 205.1 | 21.0 | 63.8 | 111.2 | 76.9 | 49.9 | 31.2 |
| Day 10 | 32.2 | 170.4 | 20.0 | 59.9 | 101.0 | 114.0 | 39.5 | 35.6 |

Functional Activities

| | C04 | C05 | C06 | C07 | C08 | C09 | C10 | C11 |
|---|---|---|---|---|---|---|---|---|
| Day 1 | 0.2 | 0.1 | 0.0 | 0.22 | 0.2 | 0.2 | 0.3 | 0.3 |
| Day 2 | 0.3 | 0.2 | 0.2 | 0.27 | 1.1 | 0.5 | 2.3 | 2.4 |
| Day 3 | 0.8 | 0.5 | 0.4 | 0.32 | 5.0 | 2.6 | 6.4 | 8.3 |
| Day 4 | 1.1 | 1.1 | 0.5 | 0.55 | 11.3 | 5.0 | 13.1 | 19.9 |
| Day 5 | 2.6 | 2.9 | 0.7 | 0.63 | 32.8 | 10.7 | 27.0 | 32.7 |
| Day 6 | 3.5 | 4.8 | 1.0 | 0.66 | 36.3 | 22.6 | 43.5 | 42.4 |
| Day 7 | 6.9 | 10.3 | 1.5 | 1.61 | 43.9 | 32.3 | 33.0 | 43.3 |
| Day 8 | 10.8 | 15.4 | 2.9 | 4.99 | 53.9 | 36.2 | 50.5 | 50.9 |
| Day 9 | 11.1 | 26.1 | 6.0 | 10.06 | 74.0 | — | 58.4 | 56.0 |
| Day 10 | 7.0 | 30.3 | 7.3 | 15.55 | 74.0 | 70.5 | 29.7 | 60.5 |

Based on the above results, C05, C07, C08 and C10 were further studied for their expression and functional activities. As shown in FIG. 2A-2D, co-transfection of the constructs with furin helped to increase functional protein titer in most cases. However, among C05, C07, C08 and C10, only C08 retained both the high expression level and functional activity.

Further, as shown in the table below, co-transfection of C08 with 5% furin yielded the highest Picogram/Cell/Day (PCD) ~1.9 in both calculations from ELISA and functional quantitative analyses.

Specific productivities based on ELISA and functional activity

| | C05 | | C07 | | C08 | | C10 | |
|---|---|---|---|---|---|---|---|---|
| Day | ELISA | Functional | ELISA | Functional | ELISA | Functional | ELISA | Functional |
| 1 | 2.04 | 0.15 | 1.13 | 0.28 | 2.09 | 1.54 | 0.56 | 0.48 |
| 2 | 2.75 | 0.71 | 2.13 | 0.71 | 2.83 | 3.41 | 0.77 | 0.82 |
| 3 | 2.32 | 0.97 | 2.29 | 0.79 | 2.59 | 3.11 | 0.61 | 0.86 |
| 4 | 1.77 | 0.93 | 1.84 | 0.89 | 2.19 | 2.62 | 0.48 | 0.89 |
| 5 | 1.54 | 0.90 | 1.74 | 0.80 | 2.18 | 2.20 | 0.52 | 0.86 |
| 6 | 1.40 | 0.89 | 1.36 | 0.69 | 2.16 | 1.83 | 0.49 | 0.73 |
| 7 | 1.11 | 0.67 | 1.03 | 0.61 | 1.92 | 1.46 | 0.37 | 0.58 |
| 8 | 1.01 | 0.70 | 0.80 | 0.44 | 1.82 | 1.83 | 0.34 | 0.51 |
| 9 | 0.85 | 0.66 | 0.78 | 0.43 | 1.70 | 1.69 | 0.36 | 0.54 |
| 10 | 0.92 | 0.78 | 0.59 | 0.43 | 1.13 | 1.65 | 0.35 | 0.55 |
| Average (Day 4-10) | 1.23 | 0.79 | 1.16 | 0.61 | 1.87 | 1.90 | 0.42 | 0.67 |

Example 3. Preparation and Testing of Additional Constructs

Based on the testing results in Example 2, this Example prepared and tested a few additional constructs, the sequences of which are provided in the tables below.

TABLE 21

Amino acid sequence of construct C12 (SEQ ID NO: 41)

Light Chain (SEQ ID NO: 6)

```
  1 ANSFL                          F WNKYKDGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Linker

```
121           R KR
```

Activation Peptide (SEQ ID NO: 12)

```
121                SVAQATSS SGEAPDSITW KPYDAADLDP TENPFDLLDF
181 NQTQPERGDN NLTR
```

Linker (SEQ ID NO: 7)
  RKRRKR

Heavy Chain Fragment (SEQ ID NO: 8)

```
181             IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

Activation Peptide without N-terminal S (SEQ ID NO: 44)

```
121                 VAQATSS SGEAPDSITW KPYDAADLDP TENPFDLLDF
181 NQTQPERGDN NLTR
```

Amino acid residue number is based on mature inactive fX (SEQ ID NO: 2)

TABLE 22

Amino acid sequence of construct C13 (SEQ ID NO: 42)

HSA (Human serum albumin, SEQ ID NO: 15)

```
DAHKSEVAHR FKDLGEENFK ALVLIAFAQY LQQSPFEDHV KLVNEVTEFA KTCVADESAE

NCDKSLHTLF GDKLCTVATL RETYGEMADC CAKQEPERNE CFLQHKDDNP NLPRLVRPEV

DVMCTAFHDN EETFLKKYLY EIARRHPYFY APELLFFAKR YKAAFTECCQ AADKAACLLP

KLDELRDEGK ASSAKQRLKC ASLQKFGERA FKAWAVARLS QRFPKAEFAE VSKLVTDLTK

VHTECCHGDL LECADDRADL AKYICENQDS ISSKLKECCE KPLLEKSHCI AEVENDEMPA

DLPSLAADFV ESKDVCKNYA EAKDVFLGMF LYEYARRHPD YSVVLLLRLA KTYETTLEKC

CAAADPHECY AKVFDEFKPL VEEPQNLIKQ NCELFEQLGE YKFQNALLVR YTKKVPQVST

PTLVEVSRNL GKVGSKCCKH PEAKRMPCAE DYLSVVLNQL CVLHEKTPVS DRVTKCCTES

LVNRRPCFSA LEVDETYVPK EFNAETFTFH ADICTLSEKE RQIKKQTALV ELVKHKPKAT

KEQLKAVMDD FAAFVEKCCK ADDKETCFAE EGKKLVAASQ AALGL
```

TABLE 22-continued

Amino acid sequence of construct C13 (SEQ ID NO: 42)

Light Chain Fragment truncated (SEQ ID NO: 13)

```
  1                                            DGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Linker (SEQ ID NO: 7)

```
    RKRRKR
```

Heavy Chain Fragment (SEQ ID NO: 8)

```
181              IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
361 NMFCAGYDTK QEDACQGDAG GPHVTRFKDT YFVTGIVSWG EGCARKGKYG IYTKVTAFLK
421 WIDRSMKTRG LPKAKSHAPE VITSSPLK
```

Amino acid residue number is based on mature inactive fX (SEQ ID NO: 2)

TABLE 23

Amino acid sequence of construct C14 (SEQ ID NO: 43)

HSA (Human serum albumin, SEQ ID NO: 15)

```
    DAHKSEVAHR FKDLGEENFK ALVLIAFAQY LQQSPFEDHV KLVNEVTEFA KTCVADESAE
    NCDKSLHTLF GDKLCTVATL RETYGEMADC CAKQEPERNE CFLQHKDDNP NLPRLVRPEV
    DVMCTAFHDN EETFLKKYLY EIARRHPYFY APELLFFAKR YKAAFTECCQ AADKAACLLP
    KLDELRDEGK ASSAKQRLKC ASLQKFGERA FKAWAVARLS QRFPKAEFAE VSKLVTDLTK
    VHTECCHGDL LECADDRADL AKYICENQDS ISSKLKECCE KPLLEKSHCI AEVENDEMPA
    DLPSLAADFV ESKDVCKNYA EAKDVFLGMF LYEYARRHPD YSVVLLLRLA KTYETTLEKC
    CAAADPHECY AKVFDEFKPL VEEPQNLIKQ NCELFEQLGE YKFQNALLVR YTKKVPQVST
    PTLVEVSRNL GKVGSKCCKH PEAKRMPCAE DYLSVVLNQL CVLHEKTPVS DRVTKCCTES
    LVNRRPCFSA LEVDETYVPK EFNAETFTFH ADICTLSEKE RQIKKQTALV ELVKHKPKAT
    KEQLKAVMDD FAAFVEKCCK ADDKETCFAE EGKKLVAASQ AALGL
```

Light Chain Fragment truncated (SEQ ID NO: 13)

```
  1                                            DGDQC ETSPCQNQGK
 61 CKDGLGEYTC TCLEGFEGKN CELFTRKLCS LDNGDCDQFC HEEQNSVVCS CARGYTLADN
121 GKACIPTGPY PCGKQTLER
```

Linker (SEQ ID NO: 7)

```
    RKRRKR
```

Heavy Chain Fragment truncated-15 (SEQ ID NO: 11)

```
181              IVGGQE CKDGECPWQA LLINEENEGF CGGTILSEFY ILTAAHCLYQ
241 AKRFKVRVGD RNTEQEEGGE AVHEVEVVIK HNRFTKETYD FDIAVLRLKT PITFRMNVAP
301 ACLPERDWAE STLMTQKTGI VSGFGRTHEK GRQSTRLKML EVPYVDRNSC KLSSSFIITQ
```

TABLE 23-continued

| Amino acid sequence of construct C14 (SEQ ID NO: 43) |
|---|
| 361 NMFCAGYDTK QEDACQGDAG GPHVTRFKDT YFVTGIVSWG EGCARKGKYG IYTKVTAFLK |
| 421 WIDRSMKTRG LPK |
| Activation Peptide (SEQ ID NO: 12) |
| 121                         SVAQATSS SGEAPDSITW KPYDAADLDP TENPFDLLDF |
| 181 NQTQPERGDN NLTR |

Amino acid residue number is based on mature inactive fX (SEQ ID NO: 2)

The domain structures of these constructs are also illustrated in FIG. 1. C12, compared to C08, has an intact heavy chain and an additional AP inserted between the EGF2 and the heavy chain. C13 is similar to C10 but with an N-terminus truncated light chain. Finally, C14 included both a HSA at the N-terminus (like C14) and an AP at the C-terminus (like C08).

Figure 3:
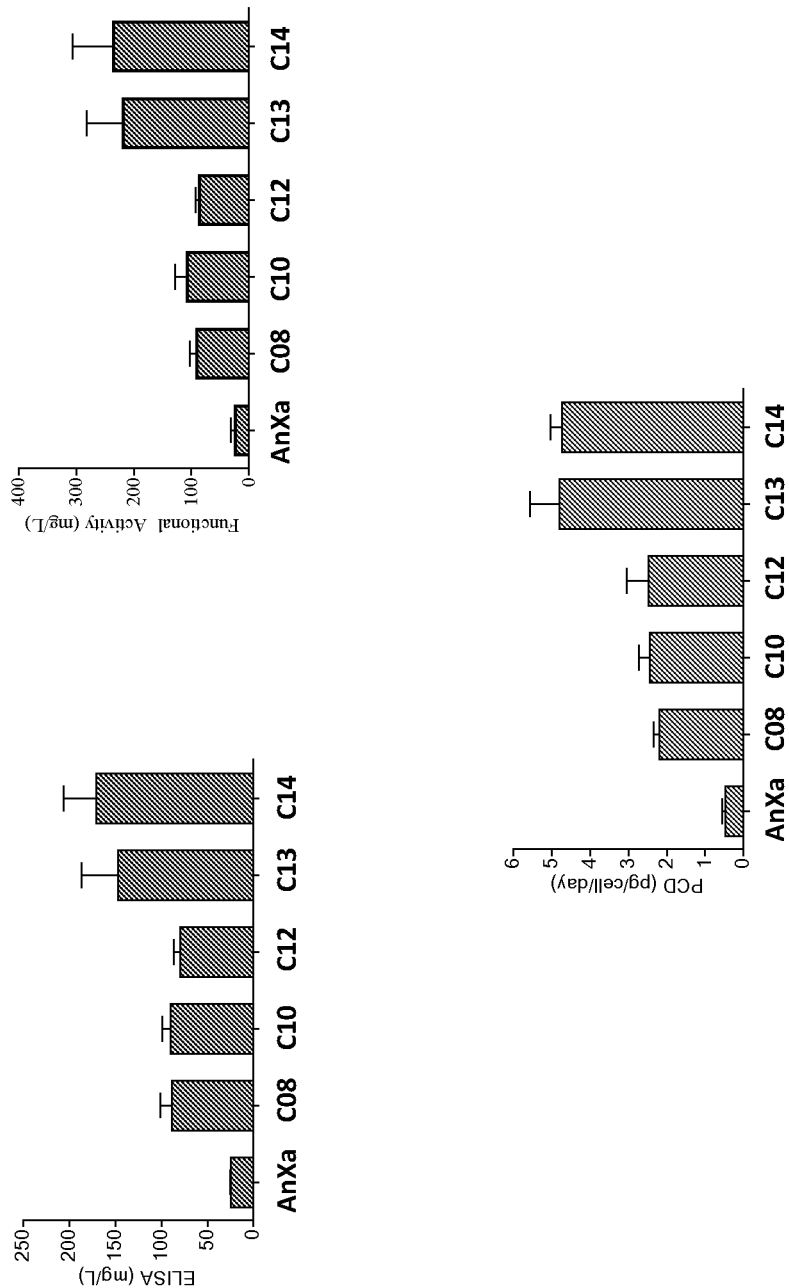
FIG. 3 shows the expression and activity testing results for C12-C14, using andexanet precursor (AnXa), C08 and C10 as references.

The expression levels and activities of these constructs, along with Andexanet precursor (AnXa), C10 and C12 as controls, were measured. The results are shown in the tables below and plotted in FIG. 3.

C13, which had a HSA fused directly to the EGF1 domain of the light chain, and C14, which further included an AP domain at the C-terminus of the heavy chain, exhibited the highest expression and activities. Interestingly, even though the only difference between C10 and C13 is that C10 further included certain amino acids from the Gla-domain (A1 to K11), C10's expression was markedly lower, suggesting that a direct fusion between the HSA and the EGF1 domain is beneficial. Moreover, the result of C12 suggests that adding an additional AP between the light chain and the heavy chain is not necessary.

ELISA (mg/L) (with each purified protein as standard)

| | AnXa | | C08 | C10 | | C12 | | C13 | | | C14 | |
|---|---|---|---|---|---|---|---|---|---|---|---|---|
| Day | n1 | n2 | n1 | n1 | n2 | n1 | n2 | n1 | n2 | n3 | n1 | n2 |
| Day 7 | — | — | 81.0 | — | 86.6 | — | — | 159.7 | 109.2 | 137.7 | — | — |
| Day 8 | — | — | 83.1 | 85.8 | 93.9 | 77.9 | 87.7 | 175.5 | 103.3 | 173.5 | — | — |
| Day 9 | — | — | 85.9 | 92.7 | 85.6 | 79.1 | 87.8 | 197.1 | 108.5 | 178.4 | 170.9 | 127.2 |
| Day 10 | 25.5 | 25.3 | 107.4 | 108.4 | 82.2 | 71.8 | 77.1 | 195.0 | 135.0 | 161.5 | 213.9 | 173.5 |
| Mean | 25.4 | | 89.4 | 90.7 | | 80.2 | | 152.9 | | | 171.4 | |
| SD | 0.1 | | 12.2 | 8.8 | | 6.3 | | 33.5 | | | 35.4 | |

Functional Activity (mg/L) (with each purified protein as standard)

| | AnXa | | C08 | C10 | | C12 | | C13 | | | C14 | |
|---|---|---|---|---|---|---|---|---|---|---|---|---|
| Day | n1 | n2 | n1 | n1 | n2 | n1 | n2 | n1 | n2 | n3 | n1 | n2 |
| Day 8 | — | 27.0 | — | 116.0 | 102.7 | 86.6 | 94.7 | — | 287.4 | 173.5 | 260.9 | 158.0 |
| Day 9 | 19.1 | 27.0 | 84.7 | 131.0 | 100.8 | 84.5 | 88.3 | — | 257.5 | 178.4 | 306.0 | 164.0 |
| Day 10 | 20.9 | 34.3 | 99.4 | 126.3 | 80.7 | — | — | 181.9 | 308.3 | 161.5 | 318.0 | 216.5 |
| Mean | 25.6 | | 92.1 | 109.6 | | 88.5 | | 221.2 | | | 237.2 | |
| SD | 6.0 | | 10.4 | 18.7 | | 4.4 | | 61.3 | | | 69.1 | |

PCD (pg/cell/day)

| | AnXa | | C08 | C10 | | C12 | | C13 | | | C14 | |
|---|---|---|---|---|---|---|---|---|---|---|---|---|
| Day | n1 | n2 | n1 | n1 | n2 | n1 | n2 | n1 | n2 | n3 | n1 | n2 |
| Day 3 | 0.57 | 0.52 | 2.26 | 2.99 | 2.40 | 3.07 | 3.28 | 4.04 | 5.13 | 4.98 | 5.04 | 4.89 |
| Day 4 | 0.57 | 0.40 | 2.02 | 2.70 | 2.24 | 2.40 | 2.72 | 4.60 | 4.68 | 4.98 | 4.61 | 4.10 |
| Day 5 | 0.47 | 0.37 | 2.19 | 2.52 | 2.11 | 2.44 | 2.55 | 4.96 | 6.58 | 5.23 | 4.67 | 4.85 |
| Day 7 | 0.53 | 0.42 | 2.34 | 2.38 | 2.33 | 1.62 | 1.87 | 3.62 | 4.94 | 3.99 | 5.03 | 4.74 |
| Mean | 0.48 | | 2.20 | 2.46 | | 2.49 | | 4.81 | | | 4.74 | |
| SD | 0.08 | | 0.13 | 0.28 | | 0.56 | | 0.75 | | | 0.30 | |

This example further demonstrates the benefit of fusing a HSA at the N-terminus of the light chain and fusing an AP domain at the C-terminus of the heavy chain in the constructs.

Example 4. Preparation and Testing of Fc Fusions

This example tested Fc fragments and fusions between the Fc fragments and a factor Xa derivative, such as Andexanet.

Two fusion constructs were prepared, as shown in Tables 25 and 26, which included the Fc fragment of Table 24, and two different signal peptides.

TABLE 24

| Fc Fragment (SEQ ID NO: 46) |
|---|
| P01857 IgG1 Human CH1-hinge-CH2-CH3 |
| ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |

TABLE 25

| Fc Fusion Construct F01 (SEQ ID NO: 47) |
|---|
| Signal peptide of fXa (SEQ ID NO: 34) |
| MGRPLHLVLL SASLAGLLLL GESLFIRREQ ANNILARVTR |
| Light Chain Fragment (SEQ ID NO: 6) |
| 1 ANSFL                     F WNKYKDGDQC ETSPCQNQGK 61 CKDGLGEYTC TCLEGFEGKN CELFTRKLCS LDNGDCDQFC HEEQNSVVCS CARGYTLADN 121 GKACIPTGPY PCGKQTLER |
| Linker (SEQ ID NO: 7) |
| RKRRKR |
| Heavy Chain Fragment (SEQ ID NO: 8) |
| 181            IVGGQE CKDGECPWQA LLINEENEGF CGGTILSEFY ILTAAHCLYQ 241 AKRFKVRVGD RNTEQEEGGE AVHEVEVVIK HNRFTKETYD FDIAVLRLKT PITFRMNVAP 301 ACLPERDWAE STLMTQKTGI VSGFGRTHEK GRQSTRLKML EVPYVDRNSC KLSSSFIITQ 361 NMFCAGYDTK QEDACQGDAG GPHVTRFKDT YFVTGIVSWG EGCARKGKYG IYTKVTAFLK 421 WIDRSMKTRG LPKAKSHAPE VITSSPLK |
| Fc fragment (SEQ ID NO: 46) |
| ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK |

Amino acid residue number is based on mature inactive fX (SEQ ID NO: 2)

TABLE 26

Fc Fusion Construct F02 (SEQ ID NO: 48)

*Signal peptide of fXa*

METDTLLLWV LLLWVPGSTG (SEQ ID NO: 45)

*Light Chain Fragment (SEQ ID NO: 6)*

| 1   | ANSFL      |            |            | F WNKYKDGDQC | ETSPCQNQGK |
|-----|------------|------------|------------|--------------|------------|
| 61  | CKDGLGEYTC | TCLEGFEGKN | CELFTRKLCS | LDNGDCDQFC HEEQNSVVCS | CARGYTLADN |
| 121 | GKACIPTGPY | PCGKQTLER  |            |              |            |

*Linker (SEQ ID NO: 7)*

RKRRKR

*Heavy Chain Fragment (SEQ ID NO: 8)*

| 181 |            | IVGGQE     | CKDGECPWQA | LLINEENEGF | CGGTILSEFY | ILTAAHCLYQ |
|-----|------------|------------|------------|------------|------------|------------|
| 241 | AKRFKVRVGD | RNTEQEEGGE | AVHEVEVVIK | HNRFTKETYD | FDIAVLRLKT | PITFRMNVAP |
| 301 | ACLPERDWAE | STLMTQKTGI | VSGFGRTHEK | GRQSTRLKML | EVPYVDRNSC | KLSSSFIITQ |
| 361 | NMFCAGYDTK | QEDACQGDAG | GPHVTRFKDT | YFVTGIVSWG | EGCARKGKYG | IYTKVTAFLK |
| 421 | WIDRSMKTRG | LPKAKSHAPE | VITSSPLK   |            |            |            |

*Fc fragment (SEQ ID NO: 46)*

ASTKGPSVFP LAPSSKSTSG GTAALGCLVK DYFPEPVTVS WNSGALTSGV

HTFPAVLQSS GLYSLSSVVT VPSSSLGTQT YICNVNHKPS NTKVDKKVEP

KSCDKTHTCP PCPAPELLGG PSVFLFPPKP KDTLMISRTP EVTCVVVDVS

HEDPEVKFNW YVDGVEVHNA KTKPREEQYN STYRVVSVLT VLHQDWLNGK

EYKCKVSNKA LPAPIEKTIS KAKGQPREPQ VYTLPPSRDE LTKNQVSLTC

LVKGFYPSDI AVEWESNGQP ENNYKTTPPV LDSDGSFFLY SKLTVDKSRW

QQGNVFSCSV MHEALHNHYT QKSLSLSPGK

Amino acid residue number is based on mature inactive fX (SEQ ID NO: 2)

The expression of these constructs were tested in transient transfections. Conditions included, chemical transfection with Expifectamine, followed by addition of enhancer and feed after 24 hrs, at 37° C., with 8% $CO_2$, 135 rpm. As shown in the results below, fXa's signal peptide (construct F01) helped increase the expression of the fusion protein.
Expression Level Measured by ELISA

|           | Fc Fragment |     | Fusion F01 |     | Fusion F02 |     |
|-----------|-------------|-----|------------|-----|------------|-----|
| Timepoint | Mean (µg/mL)| SD  | Mean (µg/mL)| SD  | Mean (µg/mL)| SD  |
| Day 1     | 2.4         | 0.2 | 0.1        | 0.0 | 0.2        | 0.0 |
| Day 2     | 5.6         | 0.9 | 1.0        | 0.1 | 1.1        | 0.2 |
| Day 3     | 12.0        | 3.0 | 1.7        | 0.3 | 2.5        | 1.4 |
| Day 4     | 14.4        | 1.9 | 3.9        | 0.0 | 2.3        | 0.4 |

-continued

|           | Fc Fragment |     | Fusion F01 |     | Fusion F02 |     |
|-----------|-------------|-----|------------|-----|------------|-----|
| Timepoint | Mean (µg/mL)| SD  | Mean (µg/mL)| SD  | Mean (µg/mL)| SD  |
| Day 5     | 15.0        | 5.3 | 5.0        | 0.0 | 4.1        | 0.6 |
| Day 6     | 15.8        | 3.9 | 6.7        | 0.3 | 4.7        | 0.8 |
| Day 7     | 24.5        | 3.9 | 9.4        | 0.3 | 6.0        | 1.1 |

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A protein comprising the amino acid sequence of formula (I):

$$LC\text{-}L1\text{-}HC\text{-}L2\text{-}AP \quad (I),$$

wherein:

LC comprises the amino acid sequence that is at least 85% identical to the amino acid sequence of SEQ ID NO:13, L1 is a peptide linker comprising a protease recognition site, HC comprises the amino acid sequence that is at least 85% identical to the amino acid sequence of SEQ ID NO:11, L2 is absent or is a peptide linker that cannot be processed by the protease recognizing the protease recognition site in L1, and AP is an activation peptide comprising the amino acid sequence that is at least 90% identical to the amino acid sequence of SEQ ID NO: 12; and wherein, when the L1 is processed by the protease, a two-chain polypeptide comprising the LC and the HC on separate chains is produced, and the two-chain polypeptide binds to a factor Xa (fXa) inhibitor.

2. The protein of claim 1, wherein the protease is furin.

3. The protein of claim 1, wherein the L1 comprises the amino acid sequence of RKR or RKRRKR (SEQ ID NO:7).

4. The protein of claim 1, wherein the L2 is 0-50 amino acid residues in length.

5. The protein of claim 4, wherein at least 50% of the amino acid residues of L2 is Gly or Ser.

6. The protein of claim 1, wherein the activation peptide comprises a glycosylation site.

7. The protein of claim 1, wherein the activation peptide comprises the amino acid sequence of SEQ ID NO: 12.

8. The protein of claim 1, wherein the protein further comprises human serum albumin (HSA) at the N-terminus of the formula (I).

9. The protein of claim 8, wherein the LC does not comprise amino acid residues 1-45 of SEQ ID NO:2.

10. The protein of claim 1, wherein the produced two-chain polypeptide has reduced capacity to assemble into a prothrombin complex as compared to a wild-type fXa.

11. The protein of claim 1, wherein the LC comprises the amino acid sequence that is at least 90% identical to the amino acid sequence of SEQ ID NO:6.

12. The protein of claim 1, wherein the produced two-chain polypeptide has reduced catalytic activity as compared to a wild-type fXa.

13. The protein of claim 1, wherein the HC comprises the amino acid sequence that is at least 90% identical to the amino acid sequence of SEQ ID NO:10.

14. The protein of claim 1, wherein the HC comprises the amino acid sequence of SEQ ID NO:11.

* * * * *

SEQUENCE LISTING

<160> NUMBER OF SEQ ID NOS: 49

<210> SEQ ID NO 1
<211> LENGTH: 488
<212> TYPE: PRT

<213> ORGANISM: Homo sapiens

<400> SEQUENCE: 1

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380

Val Asp Arg Asn Ser Cys Lys Leu Ser Ser Ser Phe Ile Ile Thr Gln
385                 390                 395                 400
```

```
Asn Met Phe Cys Ala Gly Tyr Asp Thr Lys Gln Glu Asp Ala Cys Gln
                405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
        435                 440                 445

Tyr Gly Ile Tyr Thr Lys Val Thr Ala Phe Leu Lys Trp Ile Asp Arg
    450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 2
<211> LENGTH: 448
<212> TYPE: PRT
<213> ORGANISM: Homo sapiens

<400> SEQUENCE: 2

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285
```

Lys Thr Pro Ile Thr Phe Arg Met Asn Val Ala Pro Ala Cys Leu Pro
            290                 295                 300

Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
            325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
            355                 360                 365

Thr Lys Gln Glu Asp Ala Cys Gln Gly Asp Ser Gly Gly Pro His Val
            370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
            405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
            435                 440                 445

<210> SEQ ID NO 3
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
            85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Ile Val Gly Gly Gln
    130                 135                 140

Glu Cys Lys Asp Gly Glu Cys Pro Trp Gln Ala Leu Leu Ile Asn Glu
145                 150                 155                 160

Glu Asn Glu Gly Phe Cys Gly Gly Thr Ile Leu Ser Glu Phe Tyr Ile
            165                 170                 175

Leu Thr Ala Ala His Cys Leu Tyr Gln Ala Lys Arg Phe Lys Val Arg
            180                 185                 190

Val Gly Asp Arg Asn Thr Glu Gln Glu Glu Gly Gly Glu Ala Val His

-continued

```
                195                 200                 205
Glu Val Glu Val Val Ile Lys His Asn Arg Phe Thr Lys Glu Thr Tyr
210                     215                 220

Asp Phe Asp Ile Ala Val Leu Arg Leu Lys Thr Pro Ile Thr Phe Arg
225                     230                 235                 240

Met Asn Val Ala Pro Ala Cys Leu Pro Glu Arg Asp Trp Ala Glu Ser
                    245                 250                 255

Thr Leu Met Thr Gln Lys Thr Gly Ile Val Ser Gly Phe Gly Arg Thr
                260                 265                 270

His Glu Lys Gly Arg Gln Ser Thr Arg Leu Lys Met Leu Glu Val Pro
            275                 280                 285

Tyr Val Asp Arg Asn Ser Cys Lys Leu Ser Ser Phe Ile Ile Thr
290                     295                 300

Gln Asn Met Phe Cys Ala Gly Tyr Asp Thr Lys Gln Glu Asp Ala Cys
305                     310                 315                 320

Gln Gly Asp Ser Gly Gly Pro His Val Thr Arg Phe Lys Asp Thr Tyr
                    325                 330                 335

Phe Val Thr Gly Ile Val Ser Trp Gly Glu Gly Cys Ala Arg Lys Gly
                340                 345                 350

Lys Tyr Gly Ile Tyr Thr Lys Val Thr Ala Phe Leu Lys Trp Ile Asp
            355                 360                 365

Arg Ser Met Lys Thr Arg Gly Leu Pro Lys Ala Lys Ser His Ala Pro
370                     375                 380

Glu Val Ile Thr Ser Ser Pro Leu Lys
385                     390
```

<210> SEQ ID NO 4
<211> LENGTH: 365
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 4

```
Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
                20                  25                  30

Glu Tyr Thr Cys Thr Cys Leu Glu Gly Phe Glu Gly Lys Asn Cys Glu
            35                  40                  45

Leu Phe Thr Arg Lys Leu Cys Ser Leu Asp Asn Gly Asp Cys Asp Gln
50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Arg Lys Arg Ile
            100                 105                 110

Val Gly Gly Gln Glu Cys Lys Asp Gly Glu Cys Pro Trp Gln Ala Leu
        115                 120                 125

Leu Ile Asn Glu Glu Asn Glu Gly Phe Cys Gly Gly Thr Ile Leu Ser
    130                 135                 140

Glu Phe Tyr Ile Leu Thr Ala Ala His Cys Leu Tyr Gln Ala Lys Arg
145                 150                 155                 160
```

```
Phe Lys Val Arg Val Gly Asp Arg Asn Thr Glu Gln Glu Glu Gly
                165                 170                 175

Glu Ala Val His Glu Val Glu Val Val Ile Lys His Asn Arg Phe Thr
            180                 185                 190

Lys Glu Thr Tyr Asp Phe Asp Ile Ala Val Leu Arg Leu Lys Thr Pro
            195                 200                 205

Ile Thr Phe Arg Met Asn Val Ala Pro Ala Cys Leu Pro Glu Arg Asp
210                 215                 220

Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
                245                 250                 255

Leu Glu Val Pro Tyr Val Asp Arg Asn Ser Cys Lys Leu Ser Ser Ser
            260                 265                 270

Phe Ile Ile Thr Gln Asn Met Phe Cys Ala Gly Tyr Asp Thr Lys Gln
            275                 280                 285

Glu Asp Ala Cys Gln Gly Asp Ala Gly Gly Pro His Val Thr Arg Phe
290                 295                 300

Lys Asp Thr Tyr Phe Val Thr Gly Ile Val Ser Trp Gly Glu Gly Cys
305                 310                 315                 320

Ala Arg Lys Gly Lys Tyr Gly Ile Tyr Thr Lys Val Thr Ala Phe Leu
                325                 330                 335

Lys Trp Ile Asp Arg Ser Met Lys Thr Arg Gly Leu Pro Lys Ala Lys
            340                 345                 350

Ser His Ala Pro Glu Val Ile Thr Ser Ser Pro Leu Lys
            355                 360                 365

<210> SEQ ID NO 5
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Ile Val Gly Gly Gln Glu Cys
            100                 105                 110

Lys Asp Gly Glu Cys Pro Trp Gln Ala Leu Leu Ile Asn Glu Glu Asn
        115                 120                 125

Glu Gly Phe Cys Gly Gly Thr Ile Leu Ser Glu Phe Tyr Ile Leu Thr
130                 135                 140

Ala Ala His Cys Leu Tyr Gln Ala Lys Arg Phe Lys Val Arg Val Gly
145                 150                 155                 160
```

```
Asp Arg Asn Thr Glu Gln Glu Gly Gly Glu Ala Val His Glu Val
            165                 170                 175

Glu Val Val Ile Lys His Asn Arg Phe Thr Lys Glu Thr Tyr Asp Phe
        180                 185                 190

Asp Ile Ala Val Leu Arg Leu Lys Thr Pro Ile Thr Phe Arg Met Asn
        195                 200                 205

Val Ala Pro Ala Cys Leu Pro Glu Arg Asp Trp Ala Glu Ser Thr Leu
    210                 215                 220

Met Thr Gln Lys Thr Gly Ile Val Ser Gly Phe Gly Arg Thr His Glu
225                 230                 235                 240

Lys Gly Arg Gln Ser Thr Arg Leu Lys Met Leu Glu Val Pro Tyr Val
                245                 250                 255

Asp Arg Asn Ser Cys Lys Leu Ser Ser Ser Phe Ile Ile Thr Gln Asn
            260                 265                 270

Met Phe Cys Ala Gly Tyr Asp Thr Lys Gln Glu Asp Ala Cys Gln Gly
        275                 280                 285

Asp Ala Gly Gly Pro His Val Thr Arg Phe Lys Asp Thr Tyr Phe Val
    290                 295                 300

Thr Gly Ile Val Ser Trp Gly Glu Gly Cys Ala Arg Lys Gly Lys Tyr
305                 310                 315                 320

Gly Ile Tyr Thr Lys Val Thr Ala Phe Leu Lys Trp Ile Asp Arg Ser
                325                 330                 335

Met Lys Thr Arg Gly Leu Pro Lys Ala Lys Ser His Ala Pro Glu Val
            340                 345                 350

Ile Thr Ser Ser Pro Leu Lys
            355

<210> SEQ ID NO 6
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg
            100                 105

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 7

Arg Lys Arg Arg Lys Arg
1               5

<210> SEQ ID NO 8
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 9
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
            35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
            115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
            195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr
225                 230

<210> SEQ ID NO 10
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
            35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
            115                 120                 125

Gly Phe Gly Arg Thr His Glu Lys Gly Arg Gln Ser Thr Arg Leu Lys

```
            130                 135                 140
Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
                195                 200                 205

Cys Ala Arg Lys Gly Lys Tyr Gly Ile Tyr Thr Lys Val Thr Ala Phe
            210                 215                 220

Leu Lys Trp Ile Asp Arg Ser Met Lys Thr Arg Gly Leu Pro Lys Ala
225                 230                 235                 240

Lys
```

<210> SEQ ID NO 11
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys
225                 230                 235
```

<210> SEQ ID NO 12
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ser Val Ala Gln Ala Thr Ser Ser Gly Glu Ala Pro Asp Ser Ile
1               5                   10                  15

Thr Trp Lys Pro Tyr Asp Ala Ala Asp Leu Asp Pro Thr Glu Asn Pro
            20                  25                  30

Phe Asp Leu Leu Asp Phe Asn Gln Thr Gln Pro Glu Arg Gly Asp Asn
        35                  40                  45

Asn Leu Thr Arg
    50

<210> SEQ ID NO 13
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Gly Asp Gln Cys Glu Thr Ser Pro Cys Gln Asn Gln Gly Lys Cys
1               5                   10                  15

Lys Asp Gly Leu Gly Glu Tyr Thr Cys Thr Cys Leu Glu Gly Phe Glu
            20                  25                  30

Gly Lys Asn Cys Glu Leu Phe Thr Arg Lys Leu Cys Ser Leu Asp Asn
        35                  40                  45

Gly Asp Cys Asp Gln Phe Cys His Glu Glu Gln Asn Ser Val Val Cys
    50                  55                  60

Ser Cys Ala Arg Gly Tyr Thr Leu Ala Asp Asn Gly Lys Ala Cys Ile
65                  70                  75                  80

Pro Thr Gly Pro Tyr Pro Cys Gly Lys Gln Thr Leu Glu Arg
                85                  90

<210> SEQ ID NO 14
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Ser Gly Gly Ser Gly Gly Ser Gly Gly Ser Gly Gly Ser Gly Gly
1               5                   10                  15

Ser Gly Gly Ser Gly Gly Ser Gly Gly Ser Gly Gly Ser Gly Ser
            20                  25                  30

<210> SEQ ID NO 15
<211> LENGTH: 585
<212> TYPE: PRT
<213> ORGANISM: Homo sapiens

<400> SEQUENCE: 15

Asp Ala His Lys Ser Glu Val Ala His Arg Phe Lys Asp Leu Gly Glu
1               5                   10                  15

```
Glu Asn Phe Lys Ala Leu Val Leu Ile Ala Phe Ala Gln Tyr Leu Gln
             20                  25                  30

Gln Ser Pro Phe Glu Asp His Val Lys Leu Val Asn Glu Val Thr Glu
         35                  40                  45

Phe Ala Lys Thr Cys Val Ala Asp Glu Ser Ala Glu Asn Cys Asp Lys
     50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
```

```
                    435                 440                 445
Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                    485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                    565                 570                 575

Ala Ala Ser Gln Ala Ala Leu Gly Leu
            580                 585
```

```
<210> SEQ ID NO 16
<211> LENGTH: 291
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16
```

```
Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                    85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                    165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
        195                 200                 205
```

```
Cys Ala Arg Lys Gly Lys Tyr Gly Ile Tyr Thr Lys Val Thr Ala Phe
210                 215                 220

Leu Lys Trp Ile Asp Arg Ser Met Lys Thr Arg Gly Leu Pro Lys Ser
225                 230                 235                 240

Val Ala Gln Ala Thr Ser Ser Gly Glu Ala Pro Asp Ser Ile Thr
                245                 250                 255

Trp Lys Pro Tyr Asp Ala Ala Asp Leu Asp Pro Thr Glu Asn Pro Phe
            260                 265                 270

Asp Leu Leu Asp Phe Asn Gln Thr Gln Pro Glu Arg Gly Asp Asn Asn
                275                 280                 285

Leu Thr Arg
    290
```

<210> SEQ ID NO 17
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
                20                  25                  30

Ser Glu Phe Tyr Ile Leu Thr Ala Ala His Cys Leu Tyr Gln Ala Lys
            35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ser
225                 230                 235                 240

Ser Gly Gly Ser Gly Gly Ser Gly Gly Ser Gly Gly Ser Gly Gly Ser
                245                 250                 255

Gly Gly Ser Gly Gly Ser Gly Gly Ser Gly Gly Ser Gly Ser Ser Val
            260                 265                 270
```

```
Ala Gln Ala Thr Ser Ser Ser Gly Glu Ala Pro Asp Ser Ile Thr Trp
            275                 280                 285

Lys Pro Tyr Asp Ala Ala Asp Leu Asp Pro Thr Glu Asn Pro Phe Asp
        290                 295                 300

Leu Leu Asp Phe Asn Gln Thr Gln Pro Glu Arg Gly Asp Asn Asn Leu
305                 310                 315                 320

Thr Arg

<210> SEQ ID NO 18
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Arg Lys Arg Ile
            100                 105                 110

Val Gly Gly Gln Glu Cys Lys Asp Gly Glu Cys Pro Trp Gln Ala Leu
        115                 120                 125

Leu Ile Asn Glu Glu Asn Glu Gly Phe Cys Gly Gly Thr Ile Leu Ser
130                 135                 140

Glu Phe Tyr Ile Leu Thr Ala Ala His Cys Leu Tyr Gln Ala Lys Arg
145                 150                 155                 160

Phe Lys Val Arg Val Gly Asp Arg Asn Thr Glu Gln Glu Glu Gly Gly
                165                 170                 175

Glu Ala Val His Glu Val Glu Val Val Ile Lys His Asn Arg Phe Thr
            180                 185                 190

Lys Glu Thr Tyr Asp Phe Asp Ile Ala Val Leu Arg Leu Lys Thr Pro
        195                 200                 205

Ile Thr Phe Arg Met Asn Val Ala Pro Ala Cys Leu Pro Glu Arg Asp
210                 215                 220

Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
                245                 250                 255

Leu Glu Val Pro Tyr Val Asp Arg Asn Ser Cys Lys Leu Ser Ser Ser
            260                 265                 270

Phe Ile Ile Thr Gln Asn Met Phe Cys Ala Gly Tyr Asp Thr Lys Gln
        275                 280                 285

Glu Asp Ala Cys Gln Gly Asp Ala Gly Gly Pro His Val Thr Arg Phe
290                 295                 300
```

Lys Asp Thr Tyr Phe Val Thr Gly Ile Val Ser Trp Gly Glu Gly Cys
305                 310                 315                 320

Ala Arg Lys Gly Lys Tyr Gly Ile Tyr Thr Lys Val Thr Ala Phe Leu
            325                 330                 335

Lys Trp Ile Asp Arg Ser Met Lys Thr
            340                 345

<210> SEQ ID NO 19
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Arg Lys Arg Ile
            100                 105                 110

Val Gly Gly Gln Glu Cys Lys Asp Gly Glu Cys Pro Trp Gln Ala Leu
        115                 120                 125

Leu Ile Asn Glu Glu Asn Glu Gly Phe Cys Gly Gly Thr Ile Leu Ser
130                 135                 140

Glu Phe Tyr Ile Leu Thr Ala Ala His Cys Leu Tyr Gln Ala Lys Arg
145                 150                 155                 160

Phe Lys Val Arg Val Gly Asp Arg Asn Thr Glu Gln Glu Glu Gly Gly
                165                 170                 175

Glu Ala Val His Glu Val Glu Val Val Ile Lys His Asn Arg Phe Thr
            180                 185                 190

Lys Glu Thr Tyr Asp Phe Asp Ile Ala Val Leu Arg Leu Lys Thr Pro
        195                 200                 205

Ile Thr Phe Arg Met Asn Val Ala Pro Ala Cys Leu Pro Glu Arg Asp
210                 215                 220

Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
                245                 250                 255

Leu Glu Val Pro Tyr Val Asp Arg Asn Ser Cys Lys Leu Ser Ser Ser
            260                 265                 270

Phe Ile Ile Thr Gln Asn Met Phe Cys Ala Gly Tyr Asp Thr Lys Gln
        275                 280                 285

Glu Asp Ala Cys Gln Gly Asp Ala Gly Gly Pro His Val Thr Arg Phe
290                 295                 300

Lys Asp Thr Tyr Phe Val Thr Gly Ile Val Ser Trp Gly Glu Gly Cys

```
                305                 310                 315                 320
Ala Arg Lys Gly Lys Tyr Gly Ile Tyr Thr Lys Val Thr Ala Phe Leu
                    325                 330                 335

Lys Trp Ile Asp Arg Ser Met Lys Thr Arg Gly Leu Pro Lys Ala Lys
                340                 345                 350

<210> SEQ ID NO 20
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Arg Lys Arg Ile
            100                 105                 110

Val Gly Gly Gln Glu Cys Lys Asp Gly Glu Cys Pro Trp Gln Ala Leu
        115                 120                 125

Leu Ile Asn Glu Glu Asn Glu Gly Phe Cys Gly Gly Thr Ile Leu Ser
    130                 135                 140

Glu Phe Tyr Ile Leu Thr Ala Ala His Cys Leu Tyr Gln Ala Lys Arg
145                 150                 155                 160

Phe Lys Val Arg Val Gly Asp Arg Asn Thr Glu Gln Glu Glu Gly Gly
                165                 170                 175

Glu Ala Val His Glu Val Glu Val Val Ile Lys His Asn Arg Phe Thr
            180                 185                 190

Lys Glu Thr Tyr Asp Phe Asp Ile Ala Val Leu Arg Leu Lys Thr Pro
        195                 200                 205

Ile Thr Phe Arg Met Asn Val Ala Pro Ala Cys Leu Pro Glu Arg Asp
    210                 215                 220

Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
                245                 250                 255

Leu Glu Val Pro Tyr Val Asp Arg Asn Ser Cys Lys Leu Ser Ser Ser
            260                 265                 270

Phe Ile Ile Thr Gln Asn Met Phe Cys Ala Gly Tyr Asp Thr Lys Gln
        275                 280                 285

Glu Asp Ala Cys Gln Gly Asp Ala Gly Gly Pro His Val Thr Arg Phe
    290                 295                 300

Lys Asp Thr Tyr Phe Val Thr Gly Ile Val Ser Trp Gly Glu Gly Cys
305                 310                 315                 320
```

```
Ala Arg Lys Gly Lys Tyr Gly Ile Tyr Thr Lys Val Thr Ala Phe Leu
            325                 330                 335

Lys Trp Ile Asp Arg Ser Met Lys Thr Arg Gly Leu Pro Lys
        340                 345                 350

<210> SEQ ID NO 21
<211> LENGTH: 405
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Ser Val Ala Gln
            100                 105                 110

Ala Thr Ser Ser Ser Gly Glu Ala Pro Asp Ser Ile Thr Trp Lys Pro
        115                 120                 125

Tyr Asp Ala Ala Asp Leu Asp Pro Thr Glu Asn Pro Phe Asp Leu Leu
130                 135                 140

Asp Phe Asn Gln Thr Gln Pro Glu Arg Gly Asp Asn Asn Leu Thr Arg
145                 150                 155                 160

Arg Lys Arg Arg Lys Arg Ile Val Gly Gly Gln Glu Cys Lys Asp Gly
                165                 170                 175

Glu Cys Pro Trp Gln Ala Leu Leu Ile Asn Glu Glu Asn Glu Gly Phe
            180                 185                 190

Cys Gly Gly Thr Ile Leu Ser Glu Phe Tyr Ile Leu Thr Ala Ala His
        195                 200                 205

Cys Leu Tyr Gln Ala Lys Arg Phe Lys Val Arg Val Gly Asp Arg Asn
210                 215                 220

Thr Glu Gln Glu Glu Gly Gly Glu Ala Val His Glu Val Glu Val Val
225                 230                 235                 240

Ile Lys His Asn Arg Phe Thr Lys Glu Thr Tyr Asp Phe Asp Ile Ala
                245                 250                 255

Val Leu Arg Leu Lys Thr Pro Ile Thr Phe Arg Met Asn Val Ala Pro
            260                 265                 270

Ala Cys Leu Pro Glu Arg Asp Trp Ala Glu Ser Thr Leu Met Thr Gln
        275                 280                 285

Lys Thr Gly Ile Val Ser Gly Phe Gly Arg Thr His Glu Lys Gly Arg
290                 295                 300

Gln Ser Thr Arg Leu Lys Met Leu Glu Val Pro Tyr Val Asp Arg Asn
305                 310                 315                 320

Ser Cys Lys Leu Ser Ser Ser Phe Ile Ile Thr Gln Asn Met Phe Cys
                325                 330                 335
```

```
Ala Gly Tyr Asp Thr Lys Gln Glu Asp Ala Cys Gln Gly Asp Ala Gly
            340                 345                 350

Gly Pro His Val Thr Arg Phe Lys Asp Thr Tyr Phe Val Thr Gly Ile
            355                 360                 365

Val Ser Trp Gly Glu Gly Cys Ala Arg Lys Gly Lys Tyr Gly Ile Tyr
    370                 375                 380

Thr Lys Val Thr Ala Phe Leu Lys Trp Ile Asp Arg Ser Met Lys Thr
385                 390                 395                 400

Arg Gly Leu Pro Lys
                405

<210> SEQ ID NO 22
<211> LENGTH: 409
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Gly Asp Gln Cys Glu Thr Ser Pro Cys Gln Asn Gln Gly Lys Cys
1               5                   10                  15

Lys Asp Gly Leu Gly Glu Tyr Thr Cys Thr Cys Leu Glu Gly Phe Glu
            20                  25                  30

Gly Lys Asn Cys Glu Leu Phe Thr Arg Lys Leu Cys Ser Leu Asp Asn
        35                  40                  45

Gly Asp Cys Asp Gln Phe Cys His Glu Glu Asn Ser Val Val Cys
    50                  55                  60

Ser Cys Ala Arg Gly Tyr Thr Leu Ala Asp Asn Gly Lys Ala Cys Ile
65                  70                  75                  80

Pro Thr Gly Pro Tyr Pro Cys Gly Lys Gln Thr Leu Glu Arg Arg Lys
                85                  90                  95

Arg Ser Val Ala Gln Ala Thr Ser Ser Ser Gly Glu Ala Pro Asp Ser
            100                 105                 110

Ile Thr Trp Lys Pro Tyr Asp Ala Ala Asp Leu Asp Pro Thr Glu Asn
        115                 120                 125

Pro Phe Asp Leu Leu Asp Phe Asn Gln Thr Gln Pro Glu Arg Gly Asp
    130                 135                 140

Asn Asn Leu Thr Arg Arg Lys Arg Arg Lys Arg Ile Val Gly Gly Gln
145                 150                 155                 160

Glu Cys Lys Asp Gly Glu Cys Pro Trp Gln Ala Leu Leu Ile Asn Glu
                165                 170                 175

Glu Asn Glu Gly Phe Cys Gly Gly Thr Ile Leu Ser Glu Phe Tyr Ile
            180                 185                 190

Leu Thr Ala Ala His Cys Leu Tyr Gln Ala Lys Arg Phe Lys Val Arg
        195                 200                 205

Val Gly Asp Arg Asn Thr Glu Gln Glu Glu Gly Gly Glu Ala Val His
    210                 215                 220

Glu Val Glu Val Val Ile Lys His Asn Arg Phe Thr Lys Glu Thr Tyr
225                 230                 235                 240

Asp Phe Asp Ile Ala Val Leu Arg Leu Lys Thr Pro Ile Thr Phe Arg
                245                 250                 255

Met Asn Val Ala Pro Ala Cys Leu Pro Glu Arg Asp Trp Ala Glu Ser
            260                 265                 270

Thr Leu Met Thr Gln Lys Thr Gly Ile Val Ser Gly Phe Gly Arg Thr
```

```
                275                 280                 285
His Glu Lys Gly Arg Gln Ser Thr Arg Leu Lys Met Leu Glu Val Pro
    290                 295                 300

Tyr Val Asp Arg Asn Ser Cys Lys Leu Ser Ser Phe Ile Ile Thr
305                 310                 315                 320

Gln Asn Met Phe Cys Ala Gly Tyr Asp Thr Lys Gln Glu Asp Ala Cys
                325                 330                 335

Gln Gly Asp Ala Gly Gly Pro His Val Thr Arg Phe Lys Asp Thr Tyr
                340                 345                 350

Phe Val Thr Gly Ile Val Ser Trp Gly Glu Gly Cys Ala Arg Lys Gly
                355                 360                 365

Lys Tyr Gly Ile Tyr Thr Lys Val Thr Ala Phe Leu Lys Trp Ile Asp
                370                 375                 380

Arg Ser Met Lys Thr Arg Gly Leu Pro Lys Ala Lys Ser His Ala Pro
385                 390                 395                 400

Glu Val Ile Thr Ser Ser Pro Leu Lys
                405

<210> SEQ ID NO 23
<211> LENGTH: 394
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Gly Asp Gln Cys Glu Thr Ser Pro Cys Gln Asn Gln Gly Lys Cys
1               5                   10                  15

Lys Asp Gly Leu Gly Glu Tyr Thr Cys Thr Cys Leu Gly Phe Glu
                20                  25                  30

Gly Lys Asn Cys Glu Leu Phe Thr Arg Lys Leu Cys Ser Leu Asp Asn
                35                  40                  45

Gly Asp Cys Asp Gln Phe Cys His Glu Glu Asn Ser Val Val Cys
50                  55                  60

Ser Cys Ala Arg Gly Tyr Thr Leu Ala Asp Asn Gly Lys Ala Cys Ile
65                  70                  75                  80

Pro Thr Gly Pro Tyr Pro Cys Gly Lys Gln Thr Leu Glu Arg Arg Lys
                85                  90                  95

Arg Ser Val Ala Gln Ala Thr Ser Ser Gly Glu Ala Pro Asp Ser
                100                 105                 110

Ile Thr Trp Lys Pro Tyr Asp Ala Ala Asp Leu Asp Pro Thr Glu Asn
                115                 120                 125

Pro Phe Asp Leu Leu Asp Phe Asn Gln Thr Gln Pro Glu Arg Gly Asp
130                 135                 140

Asn Asn Leu Thr Arg Arg Lys Arg Arg Lys Arg Ile Val Gly Gly Gln
145                 150                 155                 160

Glu Cys Lys Asp Gly Glu Cys Pro Trp Gln Ala Leu Leu Ile Asn Glu
                165                 170                 175

Glu Asn Glu Gly Phe Cys Gly Gly Thr Ile Leu Ser Glu Phe Tyr Ile
                180                 185                 190

Leu Thr Ala Ala His Cys Leu Tyr Gln Ala Lys Arg Phe Lys Val Arg
                195                 200                 205

Val Gly Asp Arg Asn Thr Glu Gln Glu Glu Gly Gly Glu Ala Val His
    210                 215                 220
```

```
Glu Val Glu Val Val Ile Lys His Asn Arg Phe Thr Lys Glu Thr Tyr
225                 230                 235                 240

Asp Phe Asp Ile Ala Val Leu Arg Leu Lys Thr Pro Ile Thr Phe Arg
            245                 250                 255

Met Asn Val Ala Pro Ala Cys Leu Pro Glu Arg Asp Trp Ala Glu Ser
        260                 265                 270

Thr Leu Met Thr Gln Lys Thr Gly Ile Val Ser Gly Phe Gly Arg Thr
    275                 280                 285

His Glu Lys Gly Arg Gln Ser Thr Arg Leu Lys Met Leu Glu Val Pro
290                 295                 300

Tyr Val Asp Arg Asn Ser Cys Lys Leu Ser Ser Ser Phe Ile Ile Thr
305                 310                 315                 320

Gln Asn Met Phe Cys Ala Gly Tyr Asp Thr Lys Gln Glu Asp Ala Cys
            325                 330                 335

Gln Gly Asp Ala Gly Gly Pro His Val Thr Arg Phe Lys Asp Thr Tyr
        340                 345                 350

Phe Val Thr Gly Ile Val Ser Trp Gly Glu Gly Cys Ala Arg Lys Gly
    355                 360                 365

Lys Tyr Gly Ile Tyr Thr Lys Val Thr Ala Phe Leu Lys Trp Ile Asp
370                 375                 380

Arg Ser Met Lys Thr Arg Gly Leu Pro Lys
385                 390

<210> SEQ ID NO 24
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Gly Asp Gln Cys Glu Thr Ser Pro Cys Gln Asn Gln Gly Lys Cys
1               5                   10                  15

Lys Asp Gly Leu Gly Glu Tyr Thr Cys Thr Cys Leu Glu Gly Phe Glu
            20                  25                  30

Gly Lys Asn Cys Glu Leu Phe Thr Arg Lys Leu Cys Ser Leu Asp Asn
        35                  40                  45

Gly Asp Cys Asp Gln Phe Cys His Glu Glu Gln Asn Ser Val Val Cys
    50                  55                  60

Ser Cys Ala Arg Gly Tyr Thr Leu Ala Asp Asn Gly Lys Ala Cys Ile
65                  70                  75                  80

Pro Thr Gly Pro Tyr Pro Cys Gly Lys Gln Thr Leu Glu Arg Ser Val
            85                  90                  95

Ala Gln Ala Thr Ser Ser Ser Gly Glu Ala Pro Asp Ser Ile Thr Trp
        100                 105                 110

Lys Pro Tyr Asp Ala Ala Asp Leu Asp Pro Thr Glu Asn Pro Phe Asp
    115                 120                 125

Leu Leu Asp Phe Asn Gln Thr Gln Pro Glu Arg Gly Asp Asn Asn Leu
130                 135                 140

Thr Arg Arg Lys Arg Arg Lys Arg Ile Val Gly Gly Gln Glu Cys Lys
145                 150                 155                 160

Asp Gly Glu Cys Pro Trp Gln Ala Leu Leu Ile Asn Glu Glu Asn Glu
            165                 170                 175

Gly Phe Cys Gly Gly Thr Ile Leu Ser Glu Phe Tyr Ile Leu Thr Ala
        180                 185                 190
```

Ala His Cys Leu Tyr Gln Ala Lys Arg Phe Lys Val Arg Val Gly Asp
            195                 200                 205

Arg Asn Thr Glu Gln Glu Gly Gly Glu Ala Val His Glu Val Glu
210                 215                 220

Val Val Ile Lys His Asn Arg Phe Thr Lys Glu Thr Tyr Asp Phe Asp
225                 230                 235                 240

Ile Ala Val Leu Arg Leu Lys Thr Pro Ile Thr Phe Arg Met Asn Val
                245                 250                 255

Ala Pro Ala Cys Leu Pro Glu Arg Asp Trp Ala Glu Ser Thr Leu Met
                260                 265                 270

Thr Gln Lys Thr Gly Ile Val Ser Gly Phe Gly Arg Thr His Glu Lys
            275                 280                 285

Gly Arg Gln Ser Thr Arg Leu Lys Met Leu Glu Val Pro Tyr Val Asp
        290                 295                 300

Arg Asn Ser Cys Lys Leu Ser Ser Ser Phe Ile Ile Thr Gln Asn Met
305                 310                 315                 320

Phe Cys Ala Gly Tyr Asp Thr Lys Gln Glu Asp Ala Cys Gln Gly Asp
                325                 330                 335

Ala Gly Gly Pro His Val Thr Arg Phe Lys Asp Thr Tyr Phe Val Thr
            340                 345                 350

Gly Ile Val Ser Trp Gly Glu Gly Cys Ala Arg Lys Gly Lys Tyr Gly
        355                 360                 365

Ile Tyr Thr Lys Val Thr Ala Phe Leu Lys Trp Ile Asp Arg Ser Met
    370                 375                 380

Lys Thr Arg Gly Leu Pro Lys
385                 390

<210> SEQ ID NO 25
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Gly Asp Gln Cys Glu Thr Ser Pro Cys Gln Asn Gln Gly Lys Cys
1               5                   10                  15

Lys Asp Gly Leu Gly Glu Tyr Thr Cys Thr Cys Leu Glu Gly Phe Glu
            20                  25                  30

Gly Lys Asn Cys Glu Leu Phe Thr Arg Lys Leu Cys Ser Leu Asp Asn
        35                  40                  45

Gly Asp Cys Asp Gln Phe Cys His Glu Glu Gln Asn Ser Val Val Cys
    50                  55                  60

Ser Cys Ala Arg Gly Tyr Thr Leu Ala Asp Asn Gly Lys Ala Cys Ile
65                  70                  75                  80

Pro Thr Gly Pro Tyr Pro Cys Gly Lys Gln Thr Leu Glu Arg Arg Lys
                85                  90                  95

Arg Arg Lys Arg Ile Val Gly Gly Gln Glu Cys Lys Asp Gly Glu Cys
            100                 105                 110

Pro Trp Gln Ala Leu Leu Ile Asn Glu Glu Asn Glu Gly Phe Cys Gly
        115                 120                 125

Gly Thr Ile Leu Ser Glu Phe Tyr Ile Leu Thr Ala Ala His Cys Leu
    130                 135                 140

Tyr Gln Ala Lys Arg Phe Lys Val Arg Val Gly Asp Arg Asn Thr Glu

```
            145                 150                 155                 160
        Gln Glu Glu Gly Gly Glu Ala Val His Glu Val Glu Val Val Ile Lys
                        165                 170                 175

His Asn Arg Phe Thr Lys Glu Thr Tyr Asp Phe Asp Ile Ala Val Leu
                        180                 185                 190

Arg Leu Lys Thr Pro Ile Thr Phe Arg Met Asn Val Ala Pro Ala Cys
                        195                 200                 205

Leu Pro Glu Arg Asp Trp Ala Glu Ser Thr Leu Met Thr Gln Lys Thr
        210                 215                 220

Gly Ile Val Ser Gly Phe Gly Arg Thr His Glu Lys Gly Arg Gln Ser
        225                 230                 235                 240

Thr Arg Leu Lys Met Leu Glu Val Pro Tyr Val Asp Arg Asn Ser Cys
                        245                 250                 255

Lys Leu Ser Ser Ser Phe Ile Ile Thr Gln Asn Met Phe Cys Ala Gly
                        260                 265                 270

Tyr Asp Thr Lys Gln Glu Asp Ala Cys Gln Gly Asp Ala Gly Gly Pro
                        275                 280                 285

His Val Thr Arg Phe Lys Asp Thr Tyr Phe Val Thr Gly Ile Val Ser
                        290                 295                 300

Trp Gly Glu Gly Cys Ala Arg Lys Gly Lys Tyr Gly Ile Tyr Thr Lys
        305                 310                 315                 320

Val Thr Ala Phe Leu Lys Trp Ile Asp Arg Ser Met Lys Thr Arg Gly
                        325                 330                 335

Leu Pro Lys Ser Val Ala Gln Ala Thr Ser Ser Ser Gly Glu Ala Pro
                        340                 345                 350

Asp Ser Ile Thr Trp Lys Pro Tyr Asp Ala Ala Asp Leu Asp Pro Thr
                        355                 360                 365

Glu Asn Pro Phe Asp Leu Leu Asp Phe Asn Gln Thr Gln Pro Glu Arg
                        370                 375                 380

Gly Asp Asn Asn Leu Thr Arg
        385                 390

<210> SEQ ID NO 26
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Gly Asp Gln Cys Glu Thr Ser Pro Cys Gln Asn Gln Gly Lys Cys
        1               5                   10                  15

Lys Asp Gly Leu Gly Glu Tyr Thr Cys Thr Cys Leu Glu Gly Phe Glu
                        20                  25                  30

Gly Lys Asn Cys Glu Leu Phe Thr Arg Lys Leu Cys Ser Leu Asp Asn
                        35                  40                  45

Gly Asp Cys Asp Gln Phe Cys His Glu Glu Gln Asn Ser Val Val Cys
                50                  55                  60

Ser Cys Ala Arg Gly Tyr Thr Leu Ala Asp Asn Gly Lys Ala Cys Ile
        65                  70                  75                  80

Pro Thr Gly Pro Tyr Pro Cys Gly Lys Gln Thr Leu Glu Arg Arg Lys
                        85                  90                  95

Arg Arg Lys Arg Ile Val Gly Gly Gln Glu Cys Lys Asp Gly Glu Cys
                        100                 105                 110
```

Pro Trp Gln Ala Leu Leu Ile Asn Glu Glu Asn Glu Gly Phe Cys Gly
            115                 120                 125

Gly Thr Ile Leu Ser Glu Phe Tyr Ile Leu Thr Ala Ala His Cys Leu
        130                 135                 140

Tyr Gln Ala Lys Arg Phe Lys Val Arg Val Gly Asp Arg Asn Thr Glu
145                 150                 155                 160

Gln Glu Glu Gly Gly Glu Ala Val His Glu Val Val Ile Lys
                165                 170                 175

His Asn Arg Phe Thr Lys Glu Thr Tyr Asp Phe Asp Ile Ala Val Leu
                180                 185                 190

Arg Leu Lys Thr Pro Ile Thr Phe Arg Met Asn Val Ala Pro Ala Cys
            195                 200                 205

Leu Pro Glu Arg Asp Trp Ala Glu Ser Thr Leu Met Thr Gln Lys Thr
        210                 215                 220

Gly Ile Val Ser Gly Phe Gly Arg Thr His Glu Lys Gly Arg Gln Ser
225                 230                 235                 240

Thr Arg Leu Lys Met Leu Glu Val Pro Tyr Val Asp Arg Asn Ser Cys
                245                 250                 255

Lys Leu Ser Ser Ser Phe Ile Ile Thr Gln Asn Met Phe Cys Ala Gly
            260                 265                 270

Tyr Asp Thr Lys Gln Glu Asp Ala Cys Gln Gly Asp Ala Gly Gly Pro
        275                 280                 285

His Val Thr Arg Phe Lys Asp Thr Tyr Phe Val Thr Gly Ile Val Ser
        290                 295                 300

Trp Gly Glu Gly Cys Ala Arg Lys Gly Lys Tyr Gly Ile Tyr Thr Lys
305                 310                 315                 320

Val Thr Ala Phe Leu Lys Trp Ile Asp Arg Ser Met Lys Thr Arg Gly
                325                 330                 335

Leu Pro Lys Ser Ser Gly Gly Ser Gly Gly Ser Gly Gly Ser Gly Gly
            340                 345                 350

Ser Gly Gly Ser Gly Gly Ser Gly Gly Ser Gly Gly Ser
        355                 360                 365

Gly Ser Ser Val Ala Gln Ala Thr Ser Ser Ser Gly Glu Ala Pro Asp
        370                 375                 380

Ser Ile Thr Trp Lys Pro Tyr Asp Ala Ala Asp Leu Asp Pro Thr Glu
385                 390                 395                 400

Asn Pro Phe Asp Leu Leu Asp Phe Asn Gln Thr Gln Pro Glu Arg Gly
            405                 410                 415

Asp Asn Asn Leu Thr Arg
            420

<210> SEQ ID NO 27
<211> LENGTH: 950
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ser Pro Phe Glu Asp His Val Lys Leu Val Asn Glu Val Thr Glu
            35                  40                  45

```
Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                    85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Asn Ser Phe Leu Phe Trp
            580                 585                 590

Asn Lys Tyr Lys Asp Gly Asp Gln Cys Glu Thr Ser Pro Cys Gln Asn
        595                 600                 605

Gln Gly Lys Cys Lys Asp Gly Leu Gly Glu Tyr Thr Cys Thr Cys Leu
    610                 615                 620

Glu Gly Phe Glu Gly Lys Asn Cys Glu Leu Phe Thr Arg Lys Leu Cys
625                 630                 635                 640

Ser Leu Asp Asn Gly Asp Cys Asp Gln Phe Cys His Glu Glu Gln Asn
                645                 650                 655

Ser Val Val Cys Ser Cys Ala Arg Gly Tyr Thr Leu Ala Asp Asn Gly
            660                 665                 670

Lys Ala Cys Ile Pro Thr Gly Pro Tyr Pro Cys Gly Lys Gln Thr Leu
        675                 680                 685

Glu Arg Arg Lys Arg Arg Lys Arg Ile Val Gly Gly Gln Glu Cys Lys
    690                 695                 700

Asp Gly Glu Cys Pro Trp Gln Ala Leu Leu Ile Asn Glu Glu Asn Glu
705                 710                 715                 720

Gly Phe Cys Gly Gly Thr Ile Leu Ser Glu Phe Tyr Ile Leu Thr Ala
                725                 730                 735

Ala His Cys Leu Tyr Gln Ala Lys Arg Phe Lys Val Arg Val Gly Asp
            740                 745                 750

Arg Asn Thr Glu Gln Glu Glu Gly Glu Ala Val His Glu Val Glu
        755                 760                 765

Val Val Ile Lys His Asn Arg Phe Thr Lys Glu Thr Tyr Asp Phe Asp
        770                 775                 780

Ile Ala Val Leu Arg Leu Lys Thr Pro Ile Thr Phe Arg Met Asn Val
785                 790                 795                 800

Ala Pro Ala Cys Leu Pro Glu Arg Asp Trp Ala Glu Ser Thr Leu Met
                805                 810                 815

Thr Gln Lys Thr Gly Ile Val Ser Gly Phe Gly Arg Thr His Glu Lys
            820                 825                 830

Gly Arg Gln Ser Thr Arg Leu Lys Met Leu Glu Val Pro Tyr Val Asp
        835                 840                 845

Arg Asn Ser Cys Lys Leu Ser Ser Phe Ile Ile Thr Gln Asn Met
        850                 855                 860

Phe Cys Ala Gly Tyr Asp Thr Lys Gln Glu Asp Ala Cys Gln Gly Asp
865                 870                 875                 880

Ala Gly Gly Pro His Val Thr Arg Phe Lys Asp Thr Tyr Phe Val Thr
```

885                 890                 895
Gly Ile Val Ser Trp Gly Glu Gly Cys Ala Arg Lys Gly Lys Tyr Gly
                900                 905                 910

Ile Tyr Thr Lys Val Thr Ala Phe Leu Lys Trp Ile Asp Arg Ser Met
            915                 920                 925

Lys Thr Arg Gly Leu Pro Lys Ala Lys Ser His Ala Pro Glu Val Ile
        930                 935                 940

Thr Ser Ser Pro Leu Lys
945                 950

<210> SEQ ID NO 28
<211> LENGTH: 935
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Arg Lys Arg Ile
            100                 105                 110

Val Gly Gly Gln Glu Cys Lys Asp Gly Glu Cys Pro Trp Gln Ala Leu
        115                 120                 125

Leu Ile Asn Glu Glu Asn Glu Gly Phe Cys Gly Gly Thr Ile Leu Ser
    130                 135                 140

Glu Phe Tyr Ile Leu Thr Ala Ala His Cys Leu Tyr Gln Ala Lys Arg
145                 150                 155                 160

Phe Lys Val Arg Val Gly Asp Arg Asn Thr Glu Gln Glu Glu Gly Gly
                165                 170                 175

Glu Ala Val His Glu Val Glu Val Val Ile Lys His Asn Arg Phe Thr
            180                 185                 190

Lys Glu Thr Tyr Asp Phe Asp Ile Ala Val Leu Arg Leu Lys Thr Pro
        195                 200                 205

Ile Thr Phe Arg Met Asn Val Ala Pro Ala Cys Leu Pro Glu Arg Asp
    210                 215                 220

Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
                245                 250                 255

Leu Glu Val Pro Tyr Val Asp Arg Asn Ser Cys Lys Leu Ser Ser Ser
            260                 265                 270

Phe Ile Ile Thr Gln Asn Met Phe Cys Ala Gly Tyr Asp Thr Lys Gln
        275                 280                 285

-continued

```
Glu Asp Ala Cys Gln Gly Asp Ala Gly Gly Pro His Val Thr Arg Phe
290                 295                 300
Lys Asp Thr Tyr Phe Val Thr Gly Ile Val Ser Trp Gly Glu Gly Cys
305                 310                 315                 320
Ala Arg Lys Gly Lys Tyr Gly Ile Tyr Thr Lys Val Thr Ala Phe Leu
            325                 330                 335
Lys Trp Ile Asp Arg Ser Met Lys Thr Arg Gly Leu Pro Lys Asp Ala
            340                 345                 350
His Lys Ser Glu Val Ala His Arg Phe Lys Asp Leu Gly Glu Glu Asn
            355                 360                 365
Phe Lys Ala Leu Val Leu Ile Ala Phe Ala Gln Tyr Leu Gln Gln Ser
370                 375                 380
Pro Phe Glu Asp His Val Lys Leu Val Asn Glu Val Thr Glu Phe Ala
385                 390                 395                 400
Lys Thr Cys Val Ala Asp Glu Ser Ala Glu Asn Cys Asp Lys Ser Leu
                405                 410                 415
His Thr Leu Phe Gly Asp Lys Leu Cys Thr Val Ala Thr Leu Arg Glu
            420                 425                 430
Thr Tyr Gly Glu Met Ala Asp Cys Cys Ala Lys Gln Glu Pro Glu Arg
            435                 440                 445
Asn Glu Cys Phe Leu Gln His Lys Asp Asp Asn Pro Asn Leu Pro Arg
450                 455                 460
Leu Val Arg Pro Glu Val Asp Val Met Cys Thr Ala Phe His Asp Asn
465                 470                 475                 480
Glu Glu Thr Phe Leu Lys Lys Tyr Leu Tyr Glu Ile Ala Arg Arg His
                485                 490                 495
Pro Tyr Phe Tyr Ala Pro Glu Leu Leu Phe Phe Ala Lys Arg Tyr Lys
            500                 505                 510
Ala Ala Phe Thr Glu Cys Cys Gln Ala Ala Asp Lys Ala Ala Cys Leu
            515                 520                 525
Leu Pro Lys Leu Asp Glu Leu Arg Asp Glu Gly Lys Ala Ser Ser Ala
530                 535                 540
Lys Gln Arg Leu Lys Cys Ala Ser Leu Gln Lys Phe Gly Glu Arg Ala
545                 550                 555                 560
Phe Lys Ala Trp Ala Val Ala Arg Leu Ser Gln Arg Phe Pro Lys Ala
                565                 570                 575
Glu Phe Ala Glu Val Ser Lys Leu Val Thr Asp Leu Thr Lys Val His
            580                 585                 590
Thr Glu Cys Cys His Gly Asp Leu Leu Glu Cys Ala Asp Asp Arg Ala
            595                 600                 605
Asp Leu Ala Lys Tyr Ile Cys Glu Asn Gln Asp Ser Ile Ser Ser Lys
610                 615                 620
Leu Lys Glu Cys Cys Glu Lys Pro Leu Leu Glu Lys Ser His Cys Ile
625                 630                 635                 640
Ala Glu Val Glu Asn Asp Glu Met Pro Ala Asp Leu Pro Ser Leu Ala
                645                 650                 655
Ala Asp Phe Val Glu Ser Lys Asp Val Cys Lys Asn Tyr Ala Glu Ala
            660                 665                 670
Lys Asp Val Phe Leu Gly Met Phe Leu Tyr Glu Tyr Ala Arg Arg His
            675                 680                 685
Pro Asp Tyr Ser Val Val Leu Leu Leu Arg Leu Ala Lys Thr Tyr Glu
690                 695                 700
Thr Thr Leu Glu Lys Cys Cys Ala Ala Ala Asp Pro His Glu Cys Tyr
```

```
                705                 710                 715                 720
Ala Lys Val Phe Asp Glu Phe Lys Pro Leu Val Glu Glu Pro Gln Asn
                    725                 730                 735

Leu Ile Lys Gln Asn Cys Glu Leu Phe Glu Gln Leu Gly Glu Tyr Lys
                740                 745                 750

Phe Gln Asn Ala Leu Leu Val Arg Tyr Thr Lys Lys Val Pro Gln Val
                755                 760                 765

Ser Thr Pro Thr Leu Val Glu Val Ser Arg Asn Leu Gly Lys Val Gly
                770                 775                 780

Ser Lys Cys Cys Lys His Pro Glu Ala Lys Arg Met Pro Cys Ala Glu
785                 790                 795                 800

Asp Tyr Leu Ser Val Val Leu Asn Gln Leu Cys Val Leu His Glu Lys
                805                 810                 815

Thr Pro Val Ser Asp Arg Val Thr Lys Cys Cys Thr Glu Ser Leu Val
                820                 825                 830

Asn Arg Arg Pro Cys Phe Ser Ala Leu Glu Val Asp Glu Thr Tyr Val
                835                 840                 845

Pro Lys Glu Phe Asn Ala Glu Thr Phe Thr Phe His Ala Asp Ile Cys
                850                 855                 860

Thr Leu Ser Glu Lys Glu Arg Gln Ile Lys Lys Gln Thr Ala Leu Val
865                 870                 875                 880

Glu Leu Val Lys His Lys Pro Lys Ala Thr Lys Glu Gln Leu Lys Ala
                    885                 890                 895

Val Met Asp Asp Phe Ala Ala Phe Val Glu Lys Cys Cys Lys Ala Asp
                    900                 905                 910

Asp Lys Glu Thr Cys Phe Ala Glu Glu Gly Lys Lys Leu Val Ala Ala
                915                 920                 925

Ser Gln Ala Ala Leu Gly Leu
                930                 935

<210> SEQ ID NO 29
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Gly Asp Gln Cys Glu Thr Ser Pro Cys Gln Asn Gln Gly Lys Cys
1               5                   10                  15

Lys Asp Gly Leu Gly Glu Tyr Thr Cys Thr Cys Leu Glu Gly Phe Glu
                20                  25                  30

Gly Lys Asn Cys Glu Leu Phe Thr Arg Lys Leu Cys Ser Leu Asp Asn
                35                  40                  45

Gly Asp Cys Asp Gln Phe Cys His Glu Glu Gln Asn Ser Val Val Cys
            50                  55                  60

Ser Cys Ala Arg Gly Tyr Thr Leu Ala Asp Asn Gly Lys Ala Cys Ile
65              70                  75                  80

Pro Thr Gly Pro Tyr Pro Cys Gly Lys Gln Thr Leu Glu Arg Ile Val
                85                  90                  95

Gly Gly Gln Glu Cys Lys Asp Gly Glu Cys Pro Trp Gln Ala Leu Leu
                100                 105                 110

Ile Asn Glu Glu Asn Glu Gly Phe Cys Gly Gly Thr Ile Leu Ser Glu
                115                 120                 125
```

```
Phe Tyr Ile Leu Thr Ala Ala His Cys Leu Tyr Gln Ala Lys Arg Phe
    130                 135                 140

Lys Val Arg Val Gly Asp Arg Asn Thr Glu Gln Glu Glu Gly Gly Glu
145                 150                 155                 160

Ala Val His Glu Val Glu Val Ile Lys His Asn Arg Phe Thr Lys
                165                 170                 175

Glu Thr Tyr Asp Phe Asp Ile Ala Val Leu Arg Leu Lys Thr Pro Ile
                180                 185                 190

Thr Phe Arg Met Asn Val Ala Pro Ala Cys Leu Pro Glu Arg Asp Trp
            195                 200                 205

Ala Glu Ser Thr Leu Met Thr Gln Lys Thr Gly Ile Val Ser Gly Phe
    210                 215                 220

Gly Arg Thr His Glu Lys Gly Arg Gln Ser Thr Arg Leu Lys Met Leu
225                 230                 235                 240

Glu Val Pro Tyr Val Asp Arg Asn Ser Cys Lys Leu Ser Ser Ser Phe
                245                 250                 255

Ile Ile Thr Gln Asn Met Phe Cys Ala Gly Tyr Asp Thr Lys Gln Glu
            260                 265                 270

Asp Ala Cys Gln Gly Asp Ala Gly Gly Pro His Val Thr Arg Phe Lys
        275                 280                 285

Asp Thr Tyr Phe Val Thr Gly Ile Val Ser Trp Gly Glu Gly Cys Ala
    290                 295                 300

Arg Lys Gly Lys Tyr Gly Ile Tyr Thr Lys Val Thr Ala Phe Leu Lys
305                 310                 315                 320

Trp Ile Asp Arg Ser Met Lys Thr Arg Gly Leu Pro Lys Ser Val Ala
                325                 330                 335

Gln Ala Thr Ser Ser Ser Gly Glu Ala Pro Asp Ser Ile Thr Trp Lys
            340                 345                 350

Pro Tyr Asp Ala Ala Asp Leu Asp Pro Thr Glu Asn Pro Phe Asp Leu
        355                 360                 365

Leu Asp Phe Asn Gln Thr Gln Pro Glu Arg Gly Asp Asn Asn Leu Thr
    370                 375                 380

Arg
385

<210> SEQ ID NO 30
<211> LENGTH: 416
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Gly Asp Gln Cys Glu Thr Ser Pro Cys Gln Asn Gln Gly Lys Cys
1               5                   10                  15

Lys Asp Gly Leu Gly Glu Tyr Thr Cys Thr Cys Leu Glu Gly Phe Glu
            20                  25                  30

Gly Lys Asn Cys Glu Leu Phe Thr Arg Lys Leu Cys Ser Leu Asp Asn
        35                  40                  45

Gly Asp Cys Asp Gln Phe Cys His Glu Glu Gln Asn Ser Val Val Cys
    50                  55                  60

Ser Cys Ala Arg Gly Tyr Thr Leu Ala Asp Asn Gly Lys Ala Cys Ile
65                  70                  75                  80

Pro Thr Gly Pro Tyr Pro Cys Gly Lys Gln Thr Leu Glu Arg Ile Val
                85                  90                  95
```

Gly Gly Gln Glu Cys Lys Asp Gly Glu Cys Pro Trp Gln Ala Leu Leu
                100                 105                 110

Ile Asn Glu Glu Asn Glu Gly Phe Cys Gly Gly Thr Ile Leu Ser Glu
            115                 120                 125

Phe Tyr Ile Leu Thr Ala Ala His Cys Leu Tyr Gln Ala Lys Arg Phe
        130                 135                 140

Lys Val Arg Val Gly Asp Arg Asn Thr Glu Gln Glu Glu Gly Gly Glu
145                 150                 155                 160

Ala Val His Glu Val Glu Val Val Ile Lys His Asn Arg Phe Thr Lys
                165                 170                 175

Glu Thr Tyr Asp Phe Asp Ile Ala Val Leu Arg Leu Lys Thr Pro Ile
            180                 185                 190

Thr Phe Arg Met Asn Val Ala Pro Ala Cys Leu Pro Glu Arg Asp Trp
        195                 200                 205

Ala Glu Ser Thr Leu Met Thr Gln Lys Thr Gly Ile Val Ser Gly Phe
    210                 215                 220

Gly Arg Thr His Glu Lys Gly Arg Gln Ser Thr Arg Leu Lys Met Leu
225                 230                 235                 240

Glu Val Pro Tyr Val Asp Arg Asn Ser Cys Lys Leu Ser Ser Ser Phe
                245                 250                 255

Ile Ile Thr Gln Asn Met Phe Cys Ala Gly Tyr Asp Thr Lys Gln Glu
            260                 265                 270

Asp Ala Cys Gln Gly Asp Ala Gly Gly Pro His Val Thr Arg Phe Lys
        275                 280                 285

Asp Thr Tyr Phe Val Thr Gly Ile Val Ser Trp Gly Glu Gly Cys Ala
    290                 295                 300

Arg Lys Gly Lys Tyr Gly Ile Tyr Thr Lys Val Thr Ala Phe Leu Lys
305                 310                 315                 320

Trp Ile Asp Arg Ser Met Lys Thr Arg Gly Leu Pro Lys Ser Ser Gly
                325                 330                 335

Gly Ser Gly Gly Ser Gly Gly Ser Gly Gly Ser Gly Gly Ser Gly Gly
            340                 345                 350

Ser Gly Gly Ser Gly Gly Ser Gly Gly Ser Gly Ser Val Ala Gln
        355                 360                 365

Ala Thr Ser Ser Ser Gly Glu Ala Pro Asp Ser Ile Thr Trp Lys Pro
    370                 375                 380

Tyr Asp Ala Ala Asp Leu Asp Pro Thr Glu Asn Pro Phe Asp Leu Leu
385                 390                 395                 400

Asp Phe Asn Gln Thr Gln Pro Glu Arg Gly Asp Asn Asn Leu Thr Arg
                405                 410                 415

<210> SEQ ID NO 31
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Glu Thr Val Phe Pro Asp Val Asp Tyr Val Asn Ser Thr Glu Ala
1               5                   10                  15

Glu Thr Ile Leu Asp Asn Ile Thr Gln Ser Thr Gln Ser Phe Asn Asp
            20                  25                  30

Phe Thr Arg

```
<210> SEQ ID NO 32
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Ser Glu Thr Ser Arg Thr Ala Phe Gly Gly Arg Arg Ala Val Pro
1               5                   10                  15

Pro Asn Asn Ser Asn Ala Ala Glu Asp Asp Leu Pro Thr Val Glu Leu
            20                  25                  30

Gln Gly Val Val Pro Arg
        35

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asp Thr Glu Asp Gln Glu Asp Gln Val Asp Pro Arg
1               5                   10

<210> SEQ ID NO 34
<211> LENGTH: 40
<212> TYPE: PRT
<213> ORGANISM: Homo sapiens

<400> SEQUENCE: 34

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg
        35                  40

<210> SEQ ID NO 35
<211> LENGTH: 24
<212> TYPE: PRT
<213> ORGANISM: Homo sapiens

<400> SEQUENCE: 35

Met Ala His Val Arg Gly Leu Gln Leu Pro Gly Cys Leu Ala Leu Ala
1               5                   10                  15

Ala Leu Cys Ser Leu Val His Ser
            20

<210> SEQ ID NO 36
<211> LENGTH: 19
<212> TYPE: PRT
<213> ORGANISM: Homo sapiens

<400> SEQUENCE: 36

Met Arg Leu Ala Val Gly Ala Leu Leu Val Cys Ala Val Leu Gly Leu
1               5                   10                  15

Cys Leu Ala
```

<210> SEQ ID NO 37
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg
        35                  40

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Gly Leu Pro Lys Ala Lys Ser His Ala Pro Glu Val Ile Thr Ser
1               5                   10                  15

Ser Pro Leu Lys
            20

<210> SEQ ID NO 39
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Asn Thr Phe Leu Glu Glu Val Arg Lys Gly Asn Leu Glu Arg Glu
1               5                   10                  15

Cys Val Glu Glu Thr Cys Ser Tyr Glu Glu Ala Phe Glu Ala Leu Glu
            20                  25                  30

Ser Ser Thr Ala Thr Asp Val Phe Trp Ala Lys Tyr Thr Ala Cys Glu
        35                  40                  45

Thr Ala Arg Thr Pro Arg Asp Lys Leu Ala Ala Cys Leu Glu Gly Asn
    50                  55                  60

Cys Ala Glu Gly Leu Gly Thr Asn Tyr Arg Gly His Val Asn Ile Thr
65                  70                  75                  80

Arg Ser Gly Ile Glu Cys Gln Leu Trp Arg Ser Arg Tyr Pro His Lys
                85                  90                  95

Pro Glu Ile Asn Ser Thr Thr His Pro Gly Ala Asp Leu Gln Glu Asn
            100                 105                 110

Phe Cys Arg Asn Pro Asp Ser Ser Thr Thr Gly Pro Trp Cys Tyr Thr
        115                 120                 125

Thr Asp Pro Thr Val Arg Arg Gln Glu Cys Ser Ile Pro Val Cys Gly
    130                 135                 140

Gln Asp Gln Val Thr Val Ala Met Thr Pro Arg
145                 150                 155

```
<210> SEQ ID NO 40
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Glu Gly Ser Ser Val Asn Leu Ser Pro Pro Leu Glu Gln Cys Val
1               5                   10                  15

Pro Asp Arg Gly Gln Gln Tyr Gln Gly Arg Leu Ala Val Thr Thr His
            20                  25                  30

Gly Leu Pro Cys Leu Ala Trp Ala Ser Ala Gln Ala Lys Ala Leu Ser
        35                  40                  45

Lys His Gln Asp Phe Asn Ser Ala Val Gln Leu Val Gly Asn Phe Cys
50                  55                  60

Arg Asn Pro Asp Gly Asp Glu Glu Gly Val Trp Cys Tyr Val Ala Gly
65                  70                  75                  80

Lys Pro Gly Asp Phe Gly Tyr Cys Asp Leu Asn Tyr Cys Glu Glu Ala
                85                  90                  95

Val Glu Glu Glu Thr Gly Asp Gly Leu Asp Glu Asp Ser Asp Arg Ala
            100                 105                 110

Ile Glu Gly Arg Thr Ala Thr Ser Glu Tyr Gln Thr Phe Phe Asn Pro
        115                 120                 125

Arg

<210> SEQ ID NO 41
<211> LENGTH: 471
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Ser Val Ala Gln
            100                 105                 110

Ala Thr Ser Ser Ser Gly Glu Ala Pro Asp Ser Ile Thr Trp Lys Pro
        115                 120                 125

Tyr Asp Ala Ala Asp Leu Asp Pro Thr Glu Asn Pro Phe Asp Leu Leu
    130                 135                 140

Asp Phe Asn Gln Thr Gln Pro Glu Arg Gly Asp Asn Asn Leu Thr Arg
145                 150                 155                 160

Arg Lys Arg Arg Lys Arg Ile Val Gly Gly Gln Glu Cys Lys Asp Gly
```

165                 170                 175
Glu Cys Pro Trp Gln Ala Leu Leu Ile Asn Glu Glu Asn Gly Phe
            180                 185                 190

Cys Gly Gly Thr Ile Leu Ser Glu Phe Tyr Ile Leu Thr Ala Ala His
            195                 200                 205

Cys Leu Tyr Gln Ala Lys Arg Phe Lys Val Arg Val Gly Asp Arg Asn
            210                 215                 220

Thr Glu Gln Glu Glu Gly Gly Glu Ala Val His Glu Val Glu Val Val
225                 230                 235                 240

Ile Lys His Asn Arg Phe Thr Lys Glu Thr Tyr Asp Phe Asp Ile Ala
                245                 250                 255

Val Leu Arg Leu Lys Thr Pro Ile Thr Phe Arg Met Asn Val Ala Pro
                260                 265                 270

Ala Cys Leu Pro Glu Arg Asp Trp Ala Glu Ser Thr Leu Met Thr Gln
                275                 280                 285

Lys Thr Gly Ile Val Ser Gly Phe Gly Arg Thr His Glu Lys Gly Arg
                290                 295                 300

Gln Ser Thr Arg Leu Lys Met Leu Glu Val Pro Tyr Val Asp Arg Asn
305                 310                 315                 320

Ser Cys Lys Leu Ser Ser Ser Phe Ile Ile Thr Gln Asn Met Phe Cys
                325                 330                 335

Ala Gly Tyr Asp Thr Lys Gln Glu Asp Ala Cys Gln Gly Asp Ala Gly
                340                 345                 350

Gly Pro His Val Thr Arg Phe Lys Asp Thr Tyr Phe Val Thr Gly Ile
                355                 360                 365

Val Ser Trp Gly Glu Gly Cys Ala Arg Lys Gly Lys Tyr Gly Ile Tyr
                370                 375                 380

Thr Lys Val Thr Ala Phe Leu Lys Trp Ile Asp Arg Ser Met Lys Thr
385                 390                 395                 400

Arg Gly Leu Pro Lys Ala Lys Ser His Ala Pro Glu Val Ile Thr Ser
                405                 410                 415

Ser Pro Leu Lys Val Ala Gln Ala Thr Ser Ser Gly Glu Ala Pro
                420                 425                 430

Asp Ser Ile Thr Trp Lys Pro Tyr Asp Ala Ala Asp Leu Asp Pro Thr
                435                 440                 445

Glu Asn Pro Phe Asp Leu Leu Asp Phe Asn Gln Thr Gln Pro Glu Arg
                450                 455                 460

Gly Asp Asn Asn Leu Thr Arg
465                 470

<210> SEQ ID NO 42
<211> LENGTH: 939
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Ser Pro Phe Glu Asp His Val Lys Leu Val Asn Glu Val Thr Glu
                35                  40                  45

```
Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
```

```
            465                 470                 475                 480
Leu Val Asn Arg Arg Pro Cys Phe Ser Ala Leu Glu Val Asp Glu Thr
                    485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Asp Gly Asp Gln Cys Glu Thr
                580                 585                 590

Ser Pro Cys Gln Asn Gln Gly Lys Cys Lys Asp Gly Leu Gly Glu Tyr
                595                 600                 605

Thr Cys Thr Cys Leu Glu Gly Phe Glu Gly Lys Asn Cys Glu Leu Phe
            610                 615                 620

Thr Arg Lys Leu Cys Ser Leu Asp Asn Gly Asp Cys Asp Gln Phe Cys
625                 630                 635                 640

His Glu Glu Gln Asn Ser Val Val Cys Ser Cys Ala Arg Gly Tyr Thr
                645                 650                 655

Leu Ala Asp Asn Gly Lys Ala Cys Ile Pro Thr Gly Pro Tyr Pro Cys
                660                 665                 670

Gly Lys Gln Thr Leu Glu Arg Arg Lys Arg Arg Ile Val Gly
                675                 680                 685

Gly Gln Glu Cys Lys Asp Gly Glu Cys Pro Trp Gln Ala Leu Leu Ile
            690                 695                 700

Asn Glu Glu Asn Glu Gly Phe Cys Gly Gly Thr Ile Leu Ser Glu Phe
705                 710                 715                 720

Tyr Ile Leu Thr Ala Ala His Cys Leu Tyr Gln Ala Lys Arg Phe Lys
                725                 730                 735

Val Arg Val Gly Asp Arg Asn Thr Glu Gln Glu Glu Gly Gly Glu Ala
                740                 745                 750

Val His Glu Val Glu Val Val Ile Lys His Asn Arg Phe Thr Lys Glu
            755                 760                 765

Thr Tyr Asp Phe Asp Ile Ala Val Leu Arg Leu Lys Thr Pro Ile Thr
            770                 775                 780

Phe Arg Met Asn Val Ala Pro Ala Cys Leu Pro Glu Arg Asp Trp Ala
785                 790                 795                 800

Glu Ser Thr Leu Met Thr Gln Lys Thr Gly Ile Val Ser Gly Phe Gly
                805                 810                 815

Arg Thr His Glu Lys Gly Arg Gln Ser Thr Arg Leu Lys Met Leu Glu
                820                 825                 830

Val Pro Tyr Val Asp Arg Asn Ser Cys Lys Leu Ser Ser Ser Phe Ile
                835                 840                 845

Ile Thr Gln Asn Met Phe Cys Ala Gly Tyr Asp Thr Lys Gln Glu Asp
            850                 855                 860

Ala Cys Gln Gly Asp Ala Gly Gly Pro His Val Thr Arg Phe Lys Asp
865                 870                 875                 880

Thr Tyr Phe Val Thr Gly Ile Val Ser Trp Gly Glu Gly Cys Ala Arg
                885                 890                 895
```

```
Lys Gly Lys Tyr Gly Ile Tyr Thr Lys Val Thr Ala Phe Leu Lys Trp
                900                 905                 910

Ile Asp Arg Ser Met Lys Thr Arg Gly Leu Pro Lys Ala Lys Ser His
            915                 920                 925

Ala Pro Glu Val Ile Thr Ser Ser Pro Leu Lys
        930                 935

<210> SEQ ID NO 43
<211> LENGTH: 976
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
```

```
              305                 310                 315                 320
        Glu Ala Lys Asp Val Phe Leu Gly Met Phe Leu Tyr Glu Tyr Ala Arg
                        325                 330                 335

Arg His Pro Asp Tyr Ser Val Val Leu Leu Leu Arg Leu Ala Lys Thr
                        340                 345                 350

Tyr Glu Thr Thr Leu Glu Lys Cys Cys Ala Ala Ala Asp Pro His Glu
                        355                 360                 365

Cys Tyr Ala Lys Val Phe Asp Glu Phe Lys Pro Leu Val Glu Glu Pro
                        370                 375                 380

Gln Asn Leu Ile Lys Gln Asn Cys Glu Leu Phe Glu Gln Leu Gly Glu
        385                 390                 395                 400

Tyr Lys Phe Gln Asn Ala Leu Leu Val Arg Tyr Thr Lys Lys Val Pro
                        405                 410                 415

Gln Val Ser Thr Pro Thr Leu Val Glu Val Ser Arg Asn Leu Gly Lys
                        420                 425                 430

Val Gly Ser Lys Cys Cys Lys His Pro Glu Ala Lys Arg Met Pro Cys
                        435                 440                 445

Ala Glu Asp Tyr Leu Ser Val Val Leu Asn Gln Leu Cys Val Leu His
                        450                 455                 460

Glu Lys Thr Pro Val Ser Asp Arg Val Thr Lys Cys Cys Thr Glu Ser
        465                 470                 475                 480

Leu Val Asn Arg Arg Pro Cys Phe Ser Ala Leu Glu Val Asp Glu Thr
                        485                 490                 495

Tyr Val Pro Lys Glu Phe Asn Ala Glu Thr Phe Thr Phe His Ala Asp
                        500                 505                 510

Ile Cys Thr Leu Ser Glu Lys Glu Arg Gln Ile Lys Lys Gln Thr Ala
                        515                 520                 525

Leu Val Glu Leu Val Lys His Lys Pro Lys Ala Thr Lys Glu Gln Leu
                        530                 535                 540

Lys Ala Val Met Asp Asp Phe Ala Ala Phe Val Glu Lys Cys Cys Lys
        545                 550                 555                 560

Ala Asp Asp Lys Glu Thr Cys Phe Ala Glu Glu Gly Lys Lys Leu Val
                        565                 570                 575

Ala Ala Ser Gln Ala Ala Leu Gly Leu Asp Gly Asp Gln Cys Glu Thr
                        580                 585                 590

Ser Pro Cys Gln Asn Gln Gly Lys Cys Lys Asp Gly Leu Gly Glu Tyr
                        595                 600                 605

Thr Cys Thr Cys Leu Glu Gly Phe Glu Gly Lys Asn Cys Glu Leu Phe
                        610                 615                 620

Thr Arg Lys Leu Cys Ser Leu Asp Asn Gly Asp Cys Asp Gln Phe Cys
        625                 630                 635                 640

His Glu Glu Gln Asn Ser Val Val Cys Ser Cys Ala Arg Gly Tyr Thr
                        645                 650                 655

Leu Ala Asp Asn Gly Lys Ala Cys Ile Pro Thr Gly Pro Tyr Pro Cys
                        660                 665                 670

Gly Lys Gln Thr Leu Glu Arg Arg Lys Arg Arg Ile Val Gly
                        675                 680                 685

Gly Gln Glu Cys Lys Asp Gly Glu Cys Pro Trp Gln Ala Leu Leu Ile
                        690                 695                 700

Asn Glu Glu Asn Glu Gly Phe Cys Gly Gly Thr Ile Leu Ser Glu Phe
        705                 710                 715                 720

Tyr Ile Leu Thr Ala Ala His Cys Leu Tyr Gln Ala Lys Arg Phe Lys
                        725                 730                 735
```

```
Val Arg Val Gly Asp Arg Asn Thr Glu Gln Glu Gly Gly Glu Ala
        740                 745                 750

Val His Glu Val Glu Val Val Ile Lys His Asn Arg Phe Thr Lys Glu
        755                 760                 765

Thr Tyr Asp Phe Asp Ile Ala Val Leu Arg Leu Lys Thr Pro Ile Thr
770                 775                 780

Phe Arg Met Asn Val Ala Pro Ala Cys Leu Pro Glu Arg Asp Trp Ala
785                 790                 795                 800

Glu Ser Thr Leu Met Thr Gln Lys Thr Gly Ile Val Ser Gly Phe Gly
                805                 810                 815

Arg Thr His Glu Lys Gly Arg Gln Ser Thr Arg Leu Lys Met Leu Glu
            820                 825                 830

Val Pro Tyr Val Asp Arg Asn Ser Cys Lys Leu Ser Ser Ser Phe Ile
            835                 840                 845

Ile Thr Gln Asn Met Phe Cys Ala Gly Tyr Asp Thr Lys Gln Glu Asp
        850                 855                 860

Ala Cys Gln Gly Asp Ala Gly Gly Pro His Val Thr Arg Phe Lys Asp
865                 870                 875                 880

Thr Tyr Phe Val Thr Gly Ile Val Ser Trp Gly Glu Gly Cys Ala Arg
                885                 890                 895

Lys Gly Lys Tyr Gly Ile Tyr Thr Lys Val Thr Ala Phe Leu Lys Trp
                900                 905                 910

Ile Asp Arg Ser Met Lys Thr Arg Gly Leu Pro Lys Ser Val Ala Gln
            915                 920                 925

Ala Thr Ser Ser Ser Gly Glu Ala Pro Asp Ser Ile Thr Trp Lys Pro
930                 935                 940

Tyr Asp Ala Ala Asp Leu Asp Pro Thr Glu Asn Pro Phe Asp Leu Leu
945                 950                 955                 960

Asp Phe Asn Gln Thr Gln Pro Glu Arg Gly Asp Asn Asn Leu Thr Arg
                965                 970                 975

<210> SEQ ID NO 44
<211> LENGTH: 51
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Val Ala Gln Ala Thr Ser Ser Ser Gly Glu Ala Pro Asp Ser Ile Thr
1               5                   10                  15

Trp Lys Pro Tyr Asp Ala Ala Asp Leu Asp Pro Thr Glu Asn Pro Phe
            20                  25                  30

Asp Leu Leu Asp Phe Asn Gln Thr Gln Pro Glu Arg Gly Asp Asn Asn
        35                  40                  45

Leu Thr Arg
    50

<210> SEQ ID NO 45
<211> LENGTH: 20
<212> TYPE: PRT
<213> ORGANISM: Homo sapiens

<400> SEQUENCE: 45

Met Glu Thr Asp Thr Leu Leu Leu Trp Val Leu Leu Leu Trp Val Pro
1               5                   10                  15
```

Gly Ser Thr Gly
        20

<210> SEQ ID NO 46
<211> LENGTH: 330
<212> TYPE: PRT
<213> ORGANISM: Homo sapiens

<400> SEQUENCE: 46

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 47
<211> LENGTH: 735
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 47

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Phe Trp Asn
        35                  40                  45

Lys Tyr Lys Asp Gly Asp Gln Cys Glu Thr Ser Pro Cys Gln Asn Gln
    50                  55                  60

Gly Lys Cys Lys Asp Gly Leu Gly Glu Tyr Thr Cys Thr Cys Leu Glu
65                  70                  75                  80

Gly Phe Glu Gly Lys Asn Cys Glu Leu Phe Thr Arg Lys Leu Cys Ser
                85                  90                  95

Leu Asp Asn Gly Asp Cys Asp Gln Phe Cys His Glu Glu Gln Asn Ser
            100                 105                 110

Val Val Cys Ser Cys Ala Arg Gly Tyr Thr Leu Ala Asp Asn Gly Lys
        115                 120                 125

Ala Cys Ile Pro Thr Gly Pro Tyr Pro Cys Gly Lys Gln Thr Leu Glu
    130                 135                 140

Arg Arg Lys Arg Arg Lys Arg Ile Val Gly Gly Gln Glu Cys Lys Asp
145                 150                 155                 160

Gly Glu Cys Pro Trp Gln Ala Leu Leu Ile Asn Glu Glu Asn Glu Gly
                165                 170                 175

Phe Cys Gly Gly Thr Ile Leu Ser Glu Phe Tyr Ile Leu Thr Ala Ala
            180                 185                 190

His Cys Leu Tyr Gln Ala Lys Arg Phe Lys Val Arg Val Gly Asp Arg
        195                 200                 205

Asn Thr Glu Gln Glu Glu Gly Gly Glu Ala Val His Glu Val Glu Val
    210                 215                 220

Val Ile Lys His Asn Arg Phe Thr Lys Glu Thr Tyr Asp Phe Asp Ile
225                 230                 235                 240

Ala Val Leu Arg Leu Lys Thr Pro Ile Thr Phe Arg Met Asn Val Ala
                245                 250                 255

Pro Ala Cys Leu Pro Glu Arg Asp Trp Ala Glu Ser Thr Leu Met Thr
            260                 265                 270

Gln Lys Thr Gly Ile Val Ser Gly Phe Gly Arg Thr His Glu Lys Gly
        275                 280                 285

Arg Gln Ser Thr Arg Leu Lys Met Leu Glu Val Pro Tyr Val Asp Arg
    290                 295                 300

Asn Ser Cys Lys Leu Ser Ser Ser Phe Ile Ile Thr Gln Asn Met Phe
305                 310                 315                 320

Cys Ala Gly Tyr Asp Thr Lys Gln Glu Asp Ala Cys Gln Gly Asp Ala
                325                 330                 335

Gly Gly Pro His Val Thr Arg Phe Lys Asp Thr Tyr Phe Val Thr Gly
            340                 345                 350

Ile Val Ser Trp Gly Glu Gly Cys Ala Arg Lys Gly Lys Tyr Gly Ile
        355                 360                 365

Tyr Thr Lys Val Thr Ala Phe Leu Lys Trp Ile Asp Arg Ser Met Lys
    370                 375                 380
```

```
Thr Arg Gly Leu Pro Lys Ala Lys Ser His Ala Pro Glu Val Ile Thr
385                 390                 395                 400

Ser Ser Pro Leu Lys Ala Ser Thr Lys Gly Pro Ser Val Phe Pro Leu
            405                 410                 415

Ala Pro Ser Ser Lys Ser Thr Ser Gly Gly Thr Ala Ala Leu Gly Cys
            420                 425                 430

Leu Val Lys Asp Tyr Phe Pro Glu Pro Val Thr Val Ser Trp Asn Ser
        435                 440                 445

Gly Ala Leu Thr Ser Gly Val His Thr Phe Pro Ala Val Leu Gln Ser
    450                 455                 460

Ser Gly Leu Tyr Ser Leu Ser Ser Val Val Thr Val Pro Ser Ser Ser
465                 470                 475                 480

Leu Gly Thr Gln Thr Tyr Ile Cys Asn Val Asn His Lys Pro Ser Asn
            485                 490                 495

Thr Lys Val Asp Lys Lys Val Glu Pro Lys Ser Cys Asp Lys Thr His
            500                 505                 510

Thr Cys Pro Pro Cys Pro Ala Pro Glu Leu Leu Gly Gly Pro Ser Val
        515                 520                 525

Phe Leu Phe Pro Pro Lys Pro Lys Asp Thr Leu Met Ile Ser Arg Thr
530                 535                 540

Pro Glu Val Thr Cys Val Val Val Asp Val Ser His Glu Asp Pro Glu
545                 550                 555                 560

Val Lys Phe Asn Trp Tyr Val Asp Gly Val Glu Val His Asn Ala Lys
            565                 570                 575

Thr Lys Pro Arg Glu Glu Gln Tyr Asn Ser Thr Tyr Arg Val Val Ser
            580                 585                 590

Val Leu Thr Val Leu His Gln Asp Trp Leu Asn Gly Lys Glu Tyr Lys
        595                 600                 605

Cys Lys Val Ser Asn Lys Ala Leu Pro Ala Pro Ile Glu Lys Thr Ile
        610                 615                 620

Ser Lys Ala Lys Gly Gln Pro Arg Glu Pro Gln Val Tyr Thr Leu Pro
625                 630                 635                 640

Pro Ser Arg Asp Glu Leu Thr Lys Asn Gln Val Ser Leu Thr Cys Leu
            645                 650                 655

Val Lys Gly Phe Tyr Pro Ser Asp Ile Ala Val Glu Trp Glu Ser Asn
            660                 665                 670

Gly Gln Pro Glu Asn Asn Tyr Lys Thr Thr Pro Pro Val Leu Asp Ser
        675                 680                 685

Asp Gly Ser Phe Phe Leu Tyr Ser Lys Leu Thr Val Asp Lys Ser Arg
    690                 695                 700

Trp Gln Gln Gly Asn Val Phe Ser Cys Ser Val Met His Glu Ala Leu
705                 710                 715                 720

His Asn His Tyr Thr Gln Lys Ser Leu Ser Leu Ser Pro Gly Lys
            725                 730                 735

<210> SEQ ID NO 48
<211> LENGTH: 715
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Glu Thr Asp Thr Leu Leu Leu Trp Val Leu Leu Leu Trp Val Pro
1               5                   10                  15
```

-continued

Gly Ser Thr Gly Ala Asn Ser Phe Leu Phe Trp Asn Lys Tyr Lys Asp
            20                  25                  30

Gly Asp Gln Cys Glu Thr Ser Pro Cys Gln Asn Gln Gly Lys Cys Lys
            35                  40                  45

Asp Gly Leu Gly Glu Tyr Thr Cys Thr Cys Leu Glu Gly Phe Glu Gly
 50                  55                  60

Lys Asn Cys Glu Leu Phe Thr Arg Lys Leu Cys Ser Leu Asp Asn Gly
 65                  70                  75                  80

Asp Cys Asp Gln Phe Cys His Glu Glu Gln Asn Ser Val Val Cys Ser
            85                  90                  95

Cys Ala Arg Gly Tyr Thr Leu Ala Asp Asn Gly Lys Ala Cys Ile Pro
            100                 105                 110

Thr Gly Pro Tyr Pro Cys Gly Lys Gln Thr Leu Glu Arg Arg Lys Arg
            115                 120                 125

Arg Lys Arg Ile Val Gly Gly Gln Glu Cys Lys Asp Gly Glu Cys Pro
 130                 135                 140

Trp Gln Ala Leu Leu Ile Asn Glu Glu Asn Glu Gly Phe Cys Gly Gly
 145                 150                 155                 160

Thr Ile Leu Ser Glu Phe Tyr Ile Leu Thr Ala Ala His Cys Leu Tyr
            165                 170                 175

Gln Ala Lys Arg Phe Lys Val Arg Val Gly Asp Arg Asn Thr Glu Gln
            180                 185                 190

Glu Glu Gly Gly Glu Ala Val His Glu Val Glu Val Ile Lys His
            195                 200                 205

Asn Arg Phe Thr Lys Glu Thr Tyr Asp Phe Asp Ile Ala Val Leu Arg
 210                 215                 220

Leu Lys Thr Pro Ile Thr Phe Arg Met Asn Val Ala Pro Ala Cys Leu
225                 230                 235                 240

Pro Glu Arg Asp Trp Ala Glu Ser Thr Leu Met Thr Gln Lys Thr Gly
            245                 250                 255

Ile Val Ser Gly Phe Gly Arg Thr His Glu Lys Gly Arg Gln Ser Thr
            260                 265                 270

Arg Leu Lys Met Leu Glu Val Pro Tyr Val Asp Arg Asn Ser Cys Lys
            275                 280                 285

Leu Ser Ser Ser Phe Ile Ile Thr Gln Asn Met Phe Cys Ala Gly Tyr
 290                 295                 300

Asp Thr Lys Gln Glu Asp Ala Cys Gln Gly Asp Ala Gly Gly Pro His
305                 310                 315                 320

Val Thr Arg Phe Lys Asp Thr Tyr Phe Val Thr Gly Ile Val Ser Trp
            325                 330                 335

Gly Glu Gly Cys Ala Arg Lys Gly Lys Tyr Gly Ile Tyr Thr Lys Val
            340                 345                 350

Thr Ala Phe Leu Lys Trp Ile Asp Arg Ser Met Lys Thr Arg Gly Leu
            355                 360                 365

Pro Lys Ala Lys Ser His Ala Pro Glu Val Ile Thr Ser Ser Pro Leu
            370                 375                 380

Lys Ala Ser Thr Lys Gly Pro Ser Val Phe Pro Leu Ala Pro Ser Ser
385                 390                 395                 400

Lys Ser Thr Ser Gly Gly Thr Ala Ala Leu Gly Cys Leu Val Lys Asp
            405                 410                 415

Tyr Phe Pro Glu Pro Val Thr Val Ser Trp Asn Ser Gly Ala Leu Thr
            420                 425                 430

```
Ser Gly Val His Thr Phe Pro Ala Val Leu Gln Ser Ser Gly Leu Tyr
            435                 440                 445

Ser Leu Ser Ser Val Val Thr Val Pro Ser Ser Ser Leu Gly Thr Gln
    450                 455                 460

Thr Tyr Ile Cys Asn Val Asn His Lys Pro Ser Asn Thr Lys Val Asp
465                 470                 475                 480

Lys Lys Val Glu Pro Lys Ser Cys Asp Lys Thr His Thr Cys Pro Pro
                485                 490                 495

Cys Pro Ala Pro Glu Leu Leu Gly Gly Pro Ser Val Phe Leu Phe Pro
            500                 505                 510

Pro Lys Pro Lys Asp Thr Leu Met Ile Ser Arg Thr Pro Glu Val Thr
            515                 520                 525

Cys Val Val Val Asp Val Ser His Glu Asp Pro Glu Val Lys Phe Asn
            530                 535                 540

Trp Tyr Val Asp Gly Val Glu Val His Asn Ala Lys Thr Lys Pro Arg
545                 550                 555                 560

Glu Glu Gln Tyr Asn Ser Thr Tyr Arg Val Val Ser Val Leu Thr Val
                565                 570                 575

Leu His Gln Asp Trp Leu Asn Gly Lys Glu Tyr Lys Cys Lys Val Ser
            580                 585                 590

Asn Lys Ala Leu Pro Ala Pro Ile Glu Lys Thr Ile Ser Lys Ala Lys
                595                 600                 605

Gly Gln Pro Arg Glu Pro Gln Val Tyr Thr Leu Pro Pro Ser Arg Asp
            610                 615                 620

Glu Leu Thr Lys Asn Gln Val Ser Leu Thr Cys Leu Val Lys Gly Phe
625                 630                 635                 640

Tyr Pro Ser Asp Ile Ala Val Glu Trp Glu Ser Asn Gly Gln Pro Glu
                645                 650                 655

Asn Asn Tyr Lys Thr Thr Pro Pro Val Leu Asp Ser Asp Gly Ser Phe
                660                 665                 670

Phe Leu Tyr Ser Lys Leu Thr Val Asp Lys Ser Arg Trp Gln Gln Gly
            675                 680                 685

Asn Val Phe Ser Cys Ser Val Met His Glu Ala Leu His Asn His Tyr
            690                 695                 700

Thr Gln Lys Ser Leu Ser Leu Ser Pro Gly Lys
705                 710                 715

<210> SEQ ID NO 49
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Lys Ser Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser Gly Ser
                20                  25                  30

Ser
```